(12) United States Patent
Chen et al.

(10) Patent No.: US 10,745,727 B2
(45) Date of Patent: *Aug. 18, 2020

(54) COMPOSITIONS AND METHODS RELATED TO NUCLEIC ACID SYNTHESIS

(71) Applicant: Nuclera Nucleics Ltd., Cambridge (GB)

(72) Inventors: Michael C. Chen, Cambridge (GB); Radu A. Lazar, Cambridge (GB); Jiahao Huang, Cambridge (GB); Gordon R. McInroy, Cambridge (GB)

(73) Assignee: Nuclera Nucleics Ltd., Cambridge (GB)

( * ) Notice: Subject to any disclaimer, the term of this patent is extended or adjusted under 35 U.S.C. 154(b) by 7 days.

This patent is subject to a terminal disclaimer.

(21) Appl. No.: 15/549,602

(22) PCT Filed: Feb. 10, 2016

(86) PCT No.: PCT/GB2016/050301
§ 371 (c)(1),
(2) Date: Aug. 8, 2017

(87) PCT Pub. No.: WO2016/128731
PCT Pub. Date: Aug. 18, 2016

(65) Prior Publication Data
US 2018/0023108 A1 Jan. 25, 2018

(30) Foreign Application Priority Data
Feb. 10, 2015 (GB) .................................. 1502152.0

(51) Int. Cl.
| C12P 19/34 | (2006.01) |
| C12N 9/12 | (2006.01) |
| C12Q 1/68 | (2018.01) |

(52) U.S. Cl.
CPC .............. *C12P 19/34* (2013.01); *C12N 9/12* (2013.01); *C12Q 1/68* (2013.01); *C12Y 207/07031* (2013.01)

(58) Field of Classification Search
None
See application file for complete search history.

(56) References Cited

U.S. PATENT DOCUMENTS
8,808,989 B1 8/2014 Efcavitch et al.

FOREIGN PATENT DOCUMENTS
WO 03050242 6/2003

OTHER PUBLICATIONS
Ngo et al. in the Protein Folding Problem and Tertiary Structure Prediction, 1994, Merz et al. (ed.), Birkhauser, Boston, MA, pp. 433 and 492-495.*

(Continued)

*Primary Examiner* — Richard G Hutson
(74) *Attorney, Agent, or Firm* — Morgan, Lewis & Bockius LLP

(57) ABSTRACT

The invention relates to the use of specific terminal deoxynucleotidyl transferase (TdT) enzymes in a method of nucleic acid synthesis, to methods of synthesizing nucleic acids, and to the use of kits comprising said enzymes in a method of nucleic acid synthesis. The invention also relates to the use of terminal deoxynucleotidyl transferases and 3'-blocked nucleotide triphosphates in a method of template independent nucleic acid synthesis.

17 Claims, 7 Drawing Sheets
Specification includes a Sequence Listing.

(56) References Cited

OTHER PUBLICATIONS

Accession W5MK82, UniprotKB Data base, Feb. 4, 2015.*
Beabealashvilli R S et al: "Nucleoside 1-29 5'-triphosphates modified at sugar residues as substrates for calf thymus terminal deoxynucleotidyl transferase and for AMU reverse transcriptase", Biochimica et Biophysica Acta . Gene Structure and Expression, Elsevier, Amsterdam, NL, vol. 868, No. 2-3, Nov. 13, 1986, pp. 136-144.
Database UniProt [Online] Nov. 16, 2011 (Nov. 16, 2011), "SubName: Full=Uncharacterized protein (ECO:00003131Ensembl:ENSSNAP00000005310);" XP002756023, retrieved from EBI accession No. UniProt:G3VQ55 Database accession No. G3VQ55 sequence.
Database UniProt [Online] 1-29 Apr. 16, 2014 (Apr. 16, 2014), "SubName: Full=Uncharacterized protein (ECO:00003131Ensembl:ENSLOCP000000087911;" XP002756024, retrieved from EBI accession No. UniProt:W5MK82 Database accession No. W5MK82 sequence.
Database UniProt [Online] Dec. 14, 2011 (Dec. 14, 2011), "SubName: Full=DNA nucleotidylexotransferase (ECO:00003131EMBL:ENB07806.1);", XP002756025, retrieved from EBI accession No. UniProt:G5BEU5 Database accession No. G5BEU5 sequence.
Database UniProt [Online] May 15, 2007 (May 15, 2007), "SubName: Full=Deoxynucleotidyltransferase, terminal (ECO:00003131EMBL:BAF51681.1); SubName: Full=Uncharacterized protein {ECO:00003131Ensembl:NSOGAP00000013496};" XP002756026, retrieved from EBI accession No. UniProt:A4PCE6 Database accession No. A4PCE6 sequence.
Database UniProt [Online] May 3, 2011 (May 3, 2011), "SubName: Full=Uncharacterized protein (ECO:00003131Ensembl:ENSSSCP000000111931;" XP002756027, retrieved from EBI accession No. UniProt:F1SBG2 Database accession No. F1SBG2 sequence.
Database UniProt [Online] Jan. 1, 1988 (Jan. 1, 1988), "RecName: Full=DNA nucleotidylexotransferase; EC=2.7.7.31; AltName: Full=Terminal addition enzyme; AltName: Full=Terminal, deoxynucleotidyltransferase; Short=TDT; Short=Terminal transferase;", XP002756028, retrieved from EBI accession No. UniProt:P06526 Database accession No. P06526 sequence.
S. M. Minhaz Ud-Dean: "A theoretical model for template-free synthesis of long 1-29 DNA sequence", Systems and Synthetic Biology, vol. 2, No. 3-4, Dec. 1, 2008, pp. 67-73.
Delarue, et al., "Crystal structures of a template-independent DNA polymerase: murine terminal deoxynucleotidyltransferase," the EMBO Journal, vol. 21, No. 3, pp. 427-439, 2002.

* cited by examiner

COMPOSITIONS AND METHODS RELATED TO NUCLEIC ACID SYNTHESIS

CROSS-REFERENCE TO RELATED APPLICATIONS

This application is the U.S. national phase, pursuant to 35 U.S.C. § 371, of PCT international application Ser. No. PCT/GB2016/050301, filed Feb. 10, 2016. PCT/GB2016/050301, claims priority to Great Britain Patent Application No. 1502152.0, filed Feb. 10, 2015. The contents of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 8, 2017, is named SAG-001_Sequesting_Listing.txt and is 31,146 byte in size.

FIELD OF THE INVENTION

The invention relates to the use of specific terminal deoxynucleotidyl transferase (TdT) enzymes in a method of nucleic acid synthesis, to methods of synthesizing nucleic acids, and to the use of kits comprising said enzymes in a method of nucleic acid synthesis. The invention also relates to the use of terminal deoxynucleotidyl transferases and 3'-blocked nucleotide triphosphates in a method of template independent nucleic acid synthesis.

BACKGROUND OF THE INVENTION

Nucleic acid synthesis is vital to modern biotechnology. The rapid pace of development in the biotechnology arena has been made possible by the scientific community's ability to artificially synthesise DNA, RNA and proteins.

Artificial DNA synthesis a £1 billion and growing market allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. While the benefits of DNA synthesis are numerous, an oft-mentioned problem prevents the further growth of the artificial DNA synthesis industry, and thus the biotechnology field. Despite being a mature technology, it is practically impossible to synthesise a DNA strand greater than 200 nucleotides in length, and most DNA synthesis companies only offer up to 120 nucleotides. In comparison, an average protein-coding gene is of the order of 2000-3000 nucleotides, and an average eukaryotic genome numbers in the billions of nucleotides. Thus, all major gene synthesis companies today rely on variations of a 'synthesise and stitch' technique, where overlapping 40-60-mer fragments are synthesised and stitched together by PCR (see Young, L. et al. (2004) Nucleic Acid Res. 32, e59). Current methods offered by the gene synthesis industry generally allow up to 3 kb in length for routine production.

The reason DNA cannot be synthesised beyond 120-200 nucleotides at a time is due to the current methodology for generating DNA, which uses synthetic chemistry (i.e., phosphoramidite technology) to couple a nucleotide one at a time to make DNA. As the efficiency of each nucleotide-coupling step is 95.0-99.5% efficient, it is mathematically impossible to synthesise DNA longer than 200 nucleotides in acceptable yields. The Venter Institute illustrated this laborious process by spending 4 years and 20 million USD to synthesise the relatively small genome of a bacterium (see Gibson, D. G. et al. (2010) Science 329, 52-56).

Known methods of DNA sequencing use template-dependent DNA polymerases to add 3'-reversibly terminated nucleotides to a growing double-stranded substrate (see, Bentley, D. R. et al. (2008) Nature 456, 53-59). In the 'sequencing-by-synthesis' process, each added nucleotide contains a dye, allowing the user to identify the exact sequence of the template strand. Albeit on double-stranded DNA, this technology is able to produce strands of between 500-1000 bps long. However, this technology is not suitable for de novo nucleic acid synthesis because of the requirement for an existing nucleic acid strand to act as a template.

Various attempts have been made to use a terminal deoxynucleotidyi transferase for controlled de novo single-stranded DNA synthesis (see Ud-Dean, S. M. M. (2009) Syst Synth Boil 2, 67-73, U.S. Pat. Nos. 5,763,594 and 8,808,989). Uncontrolled de novo single-stranded DNA synthesis, as opposed to controlled, takes advantage of TdT's deoxynucleotide triphosphate (dNTP) 3'tailing properties on single-stranded DNA to create, for example, homopolymeric adaptor sequences for next-generation sequencing library preparation (see Roychoudhury R., et al. (1976) Nucleic Acids Res 3, 101-116 and WO 2003/050242). A reversible deoxynucleotide triphosphate termination technology needs to be employed to prevent uncontrolled addition of dNTPs to the 3'-end of a growing DNA strand. The development of a controlled single-stranded DNA synthesis process through Td1 would be invaluable to in situ DNA synthesis for gene assembly or hybridization microarrays as it removes the need for an anhydrous environment and allows the use of various polymers incompatible with organic solvents (see Blanchard, A. P. (1996) Biosens Bioelectron 11, 687-690 and U.S. Pat. No. 7,534,561).

However, TdT has not been shown to efficiently add nucleotide triphosphates containing 3'-O reversibly terminating moieties for building up a nascent single-stranded DNA chain necessary for a de novo synthesis cycle. A 3'-O reversible terminating moiety would prevent a terminal transferase like TdT from catalysing the nucleotide transferase reaction between the 3'-end of a growing DNA strand and the 5'-triphosphate of an incoming nucleotide triphosphate. Data is presented herein which demonstrates that the widely commercially available recombinant TdT sourced from calf thymus is unable to add 3'-O-terminated nucleotide triphosphates in a quantitative fashion (see FIG. 3). In previous reports, the TdT specifically mentioned is recombinant TdT from calf thymus (see Ud-Dean, S. M. M. (2009) Syst Synth Boil 2, 67-73, U.S. Pat. Nos. 5,763,594 and 8,808,989) or uses a different reversible terminating mechanism not located on the 3' end of the deoxyribose moiety (see U.S. Pat. No. 8,808,989).

Most DNA and RNA polymerases contain highly selective sugar steric gates to tightly discriminate between deoxyribose and ribose nucleotide triphosphate substrates (see Joyce C. M. (1997) Proc Natl Acad Sci 94, 1619-22). The result of this sugar steric gate is the enormous challenge of finding and/or engineering polymerases to accept sugar variants for biotechnology reasons, such as sequencing-by-synthesis (see Metzker M. L. (2010) *Nat Rev Genet* 11, 31-46 and U.S. Pat. No. 8,460,910). The challenge of finding a polymerase that accepts a 3'-O reversibly terminating nucleotide is so large, various efforts have been made to create reversible terminating nucleotides where the polymerase termination mechanism is located on the nitrogenous base of the terminating nucleotide (see Gardner, A. F. (2012) *Nucleic Acids Res* 40, 7404-15 and U.S. Pat. No. 8,889,860).

There is therefore a need to identify terminal deoxynucleotidyl transferases that readily incorporate 3'-O reversibly terminated nucleotides and modified said terminal deoxynucleotidyl transferases to incorporate 3'-O reversibly terminated nucleotides in a fashion useful for biotechnology and single-stranded DNA synthesis processes in order to provide an improved method of nucleic acid synthesis that is able to overcome the problems associated with currently available methods.

SUMMARY OF THE INVENTION

According to a first aspect of the invention, there is provided the use of a terminal deoxynucleotidyl transferase (TdT) enzyme comprising an amino acid sequence selected from either: (a) any one of SEQ ID NOS: 1 to 5 and 8 or a functional equivalent or fragment thereof having at least 20% sequence homology to said amino acid sequence; or (b) a modified derivative of SEQ ID NO: 6; in a method of nucleic acid synthesis.

According to a second aspect of the invention, there is provided a method of nucleic acid synthesis, which comprises the steps of:

(a) providing an initiator sequence;

(b) adding a 3'-blocked nucleotide triphosphate to said initiator sequence in the presence of a terminal deoxynucleotidyl transferase (TdT) as defined in the first aspect of the invention;

(c) removal of all reagents from the initiator sequence;

(d) cleaving the blocking group from the 3'-blocked nucleotide triphosphate in the presence of a cleaving agent;

(e) removal of the cleaving agent.

According to a further aspect of the invention, there is provided the use of a kit in a method of nucleic acid synthesis, wherein said kit comprises a TdT as defined in the first or second aspects of the invention optionally in combination with one or more components selected from: an initiator sequence, one or more 3'-blocked nucleotide triphosphates, inorganic pyrophosphatase, such as purified, recombinant inorganic pyrophosphatase from *Saccharomyces cerevisiae*, and a cleaving agent; further optionally together with instructions for use of the kit in accordance with any of the methods defined herein.

According to a further aspect of the invention, there is provided the use of a 3'-blocked nucleotide triphosphate in a method of template independent nucleic acid synthesis, wherein the 3'-blocked nucleotide triphosphate is selected from a compound of formula (I), (II), (III) or (IV):

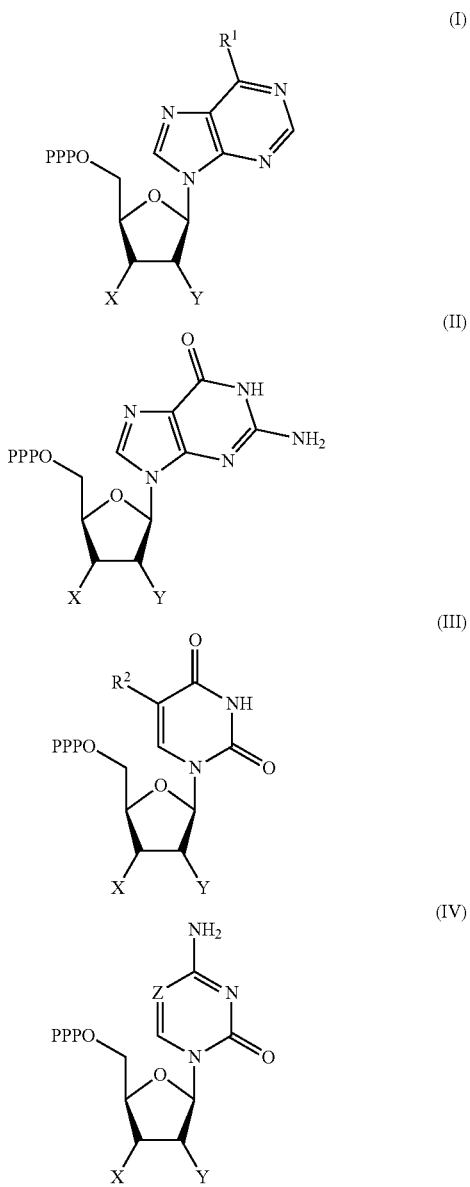

wherein
R$^1$ represents NR$^a$R$^b$, wherein R$^a$ and R$^b$ independently represent hydrogen or C$_{1-6}$ alkyl,
R$^2$ represents hydrogen, C$_{1-6}$ alkyl, C$_{1-6}$ alkoxy, COH or COOH.
X represents C$_{1-6}$ alkyl, NH$_2$, N$_3$ or —OR$^3$,
R$^3$ represents C$_{1-6}$ alkyl, CH$_2$N$_3$, NH$_2$ or allyl,
Y represents hydrogen, halogen or hydroxyl, and
Z represents CR$^4$ or N, wherein R$^4$ represents hydrogen, C$_{1-6}$ alkyl, C$_{1-6}$alkoxy, COH or COOH.

According to a further aspect of the invention, there is provided the use of inorganic pyrophosphatase in a method of nucleic acid synthesis.

DETAILED DESCRIPTION OF THE INVENTION

Figure 1:
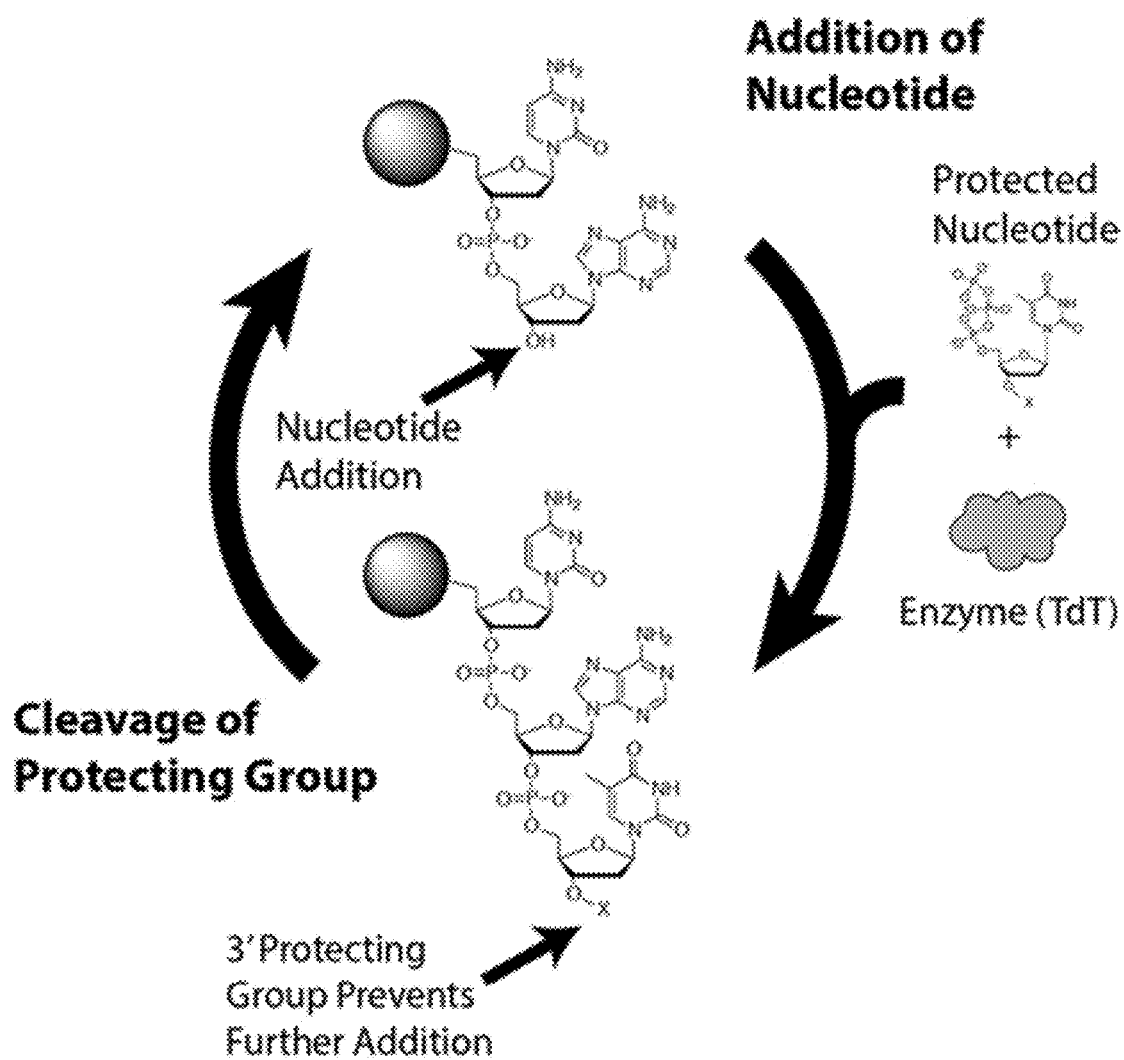
FIG. 1: Schematic of enzymatic DNA synthesis process. Starting from the top of the diagram, an immobilised strand of DNA with a deprotected 3'-end is exposed to an extension mixture composed of TdT, a base-specific 3'-blocked nucleotide triphosphate, inorganic pyrophosphatase to reduce the buildup of inorganic pyrophosphate, and appropriate buffers/salts for optimal enzyme activity and stability. The protein adds one protected nucleotide to the immobilised DNA strand (bottom of diagram). The extension mixture is then removed with wash mixture and optionally recycled. The immobilised (n+1) DNA strand is then washed with a cleavage mixture to cleave the 3'-protecting group, enabling reaction in the next cycle. In the cleavage mixture, denaturant may be present to disrupt any secondary structures. During this step, the temperature may be raised to assist in cleavage and disruption of secondary structures. The immobilised DNA is treated with wash mixture to remove leftover cleavage mixture. Steps 1-4 may be repeated with an appropriate nucleotide triphosphate until the desired oligonucleotide sequence is achieved.

According to a first aspect of the invention, there is provided the use of a terminal deoxynucleotidyl transferase (TdT) enzyme comprising an amino acid sequence selected from either: (a) any one of SEQ ID NOS: 1 to 5 and 8 or a functional equivalent or fragment thereof having at least 20% sequence homology to said amino acid sequence; or (b) a modified derivative of SEQ ID NO: 6; in a method of nucleic acid synthesis.

According to one particular aspect of the invention which may be mentioned, there is provided the use of a terminal deoxynucleotidyl transferase (TdT) enzyme comprising an amino acid sequence selected from either: (a) any one of SEQ ID NOS: 1 to 5 or a functional equivalent or fragment thereof having at least 20% sequence homology to said amino acid sequence; or (b) a modified derivative of SEQ ID NO: 6; in a method of nucleic acid synthesis.

The present invention relates to the identification of never before studied terminal deoxynucleotidyl transferases that surprisingly have the ability to incorporate deoxynucleotide triphosphates with large 3'-O reversibly terminating moieties.

Since commercially available recombinant TdT sourced from calf thymus does not readily incorporate 3'-O reversibly terminated nucleotides, it is most unexpected that the present inventors have located a terminal deoxynucleotidyl transferase, which is a DNA polymerase, to accept a 3'-O reversibly terminating nucleotide, such as dNTPs modified with a 3'-O-azidomethyl.

Furthermore, the present invention relates to engineered terminal deoxynucleotidyl transferases, which achieve a substantial increase in incorporation rates of dNTPs containing 3'-O reversibly terminating moieties to be useful for the controlled de novo synthesis of single-stranded DNA.

As controlled de novo single-stranded DNA synthesis is an additive process, coupling efficiency is extremely important to obtaining practically useful yields of final single-stranded DNA product for use in applications such as gene assembly or hybridization microarrays. Thus, the present invention relates to the identification of TdT orthologs with the capability to add 3'-O reversibly terminated nucleotides, and also an engineered variant of the TdT ortholog that adds 3'-O reversibly terminated nucleotides in a quantitative fashion that is practically useful for a single-stranded DNA synthesis process.

The use described herein has significant advantages, such as the ability to rapidly produce long lengths of DNA while still maintaining high yields and without using any toxic organic solvents.

In one embodiment, the terminal deoxynucleotidyl transferase (TdT) enzyme comprises an amino acid sequence selected from any one of SEQ ID NOS: 1 to 5 and 8 or a functional equivalent or fragment thereof having at least 20% sequence homology to said amino acid sequence.

In a further embodiment, the terminal deoxynucleotidyl transferase (TdT) enzyme comprises an amino acid sequence selected from any one of SEQ ID NOS: 1 to 5 or a functional equivalent or fragment thereof having at least 20% sequence homology to said amino acid sequence.

In a further embodiment, the terminal deoxynucleotidyl transferase (TdT) enzyme comprises an amino acid sequence selected from SEQ ID NO: 1. The amino acid sequence of SEQ ID NO: 1 is the terminal deoxynucleotidyl transferase (TdT) sequence from *Sarcophilus harrisii* (UniProt: G3VQ55). *Sarcophilus harrisii* (also known as the Tasmanian devil) is a carnivorous marsupial of the family Dasyuridae, now found in the wild only on the Australian island state of Tasmania.

In a further embodiment, the terminal deoxynucleotidyl transferase (TdT) enzyme comprises an amino acid sequence selected from SEQ ID NO: 2. The amino acid sequence of SEQ ID NO: 2 is the terminal deoxynucleotidyl transferase (TdT) sequence from *Lepisosteus oculatus* (UniProt: W5MK82). *Lepisosteus oculatus* (also known as the spotted gar) is a primitive freshwater fish of the family Lepisosteidae, native to North America from the Lake Erie and southern Lake Michigan drainages south through the Mississippi River basin to Gulf Slope drainages, from lower Apalachicola River in Florida to Nueces River in Texas, USA.

In a further embodiment, the terminal deoxynucleotidyl transferase (TdT) enzyme comprises an amino acid sequence selected from SEQ ID NO: 3. The amino acid sequence of SEQ ID NO: 3 is the terminal deoxynucleotidyl transferase (TdT) sequence from *Chinchilla lanigera* (NCBI Reference Sequence: XP_005407631.1; http://www.ncbi.nlm.nih.gov/protein/533189443). *Chinchilla lanigera* (also known as the long-tailed chinchilla, Chilean, coastal, common chinchilla, or lesser chinchilla), is one of two species of rodents from the genus Chinchilla, the other species being *Chinchilla chinchilla*.

In a further embodiment, the terminal deoxynucleotidyl transferase (TdT) enzyme comprises an amino acid sequence selected from SEQ ID NO: 4. The amino acid sequence of SEQ ID NO: 4 is the terminal deoxynucleotidyl transferase (TdT) sequence from *Otolemur garnettii* (UniProt: A4PCE6). *Otolemur garnettii* (also known as the northern greater galago, Garnett's greater galago or small-eared greater galago), is a nocturnal, arboreal primate endemic to Africa.

In a further embodiment, the terminal deoxynucleotidyl transferase (TdT) enzyme comprises an amino acid sequence selected from SEQ ID NO: 5. The amino acid sequence of SEQ ID NO: 5 is the terminal deoxynucleotidyl transferase (TdT) sequence from *Sus scrofa* (UniProt: F1SBG2). *Sus scrofa* (also known as the wild boar, wild swine or Eurasian wild pig) is a suid native to much of Eurasia, North Africa and the Greater Sunda Islands.

Figure 4:
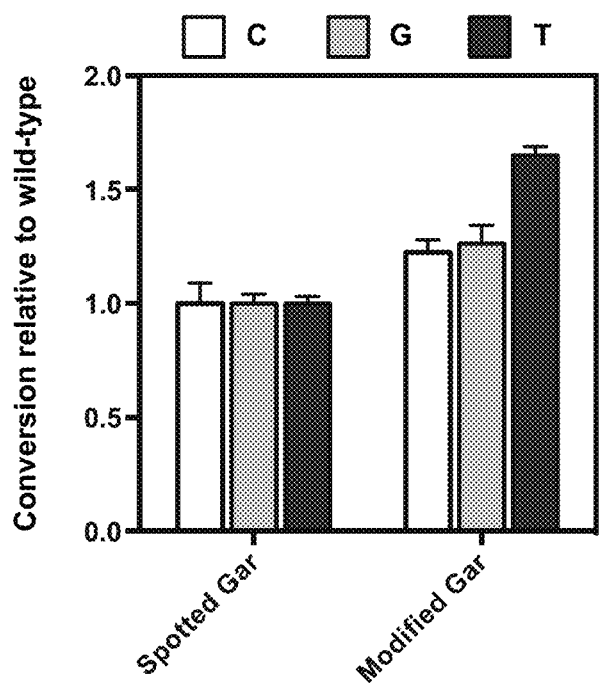
FIG. 4: An engineered variant of *Lepisosteus oculatus* TdT shows improved activity over the wild-type *Lepisoteus oculatus* TdT. A DNA initiator strand was incubated with 1 mM 3'-reversibly blocked dNTP at 37° C. for 20 minutes with required salts as described previously. Addition of the dNTP was measured by PAGE and the conversion relative to wild-type TdT was plotted.

In a further embodiment, the terminal deoxynucleotidyl transferase (TdT) enzyme comprises an amino acid sequence selected from SEQ ID NO: 8. The amino acid sequence of SEQ ID NO: 8 is a variant of SEQ ID NO: 2 which has been engineered for improved activity by alteration of the amino acid sequence. Data are provided in Example 3 and FIG. 4, which demonstrate the benefits of engineered variants, such as SEQ ID NO: 8, over the wild-type SEQ ID NO: 2.

In a further embodiment, the terminal deoxynucleotidyl transferase (TdT) enzyme comprises an amino acid sequence selected from SEQ ID NOS: 1, 2 or 8.

Figure 3:
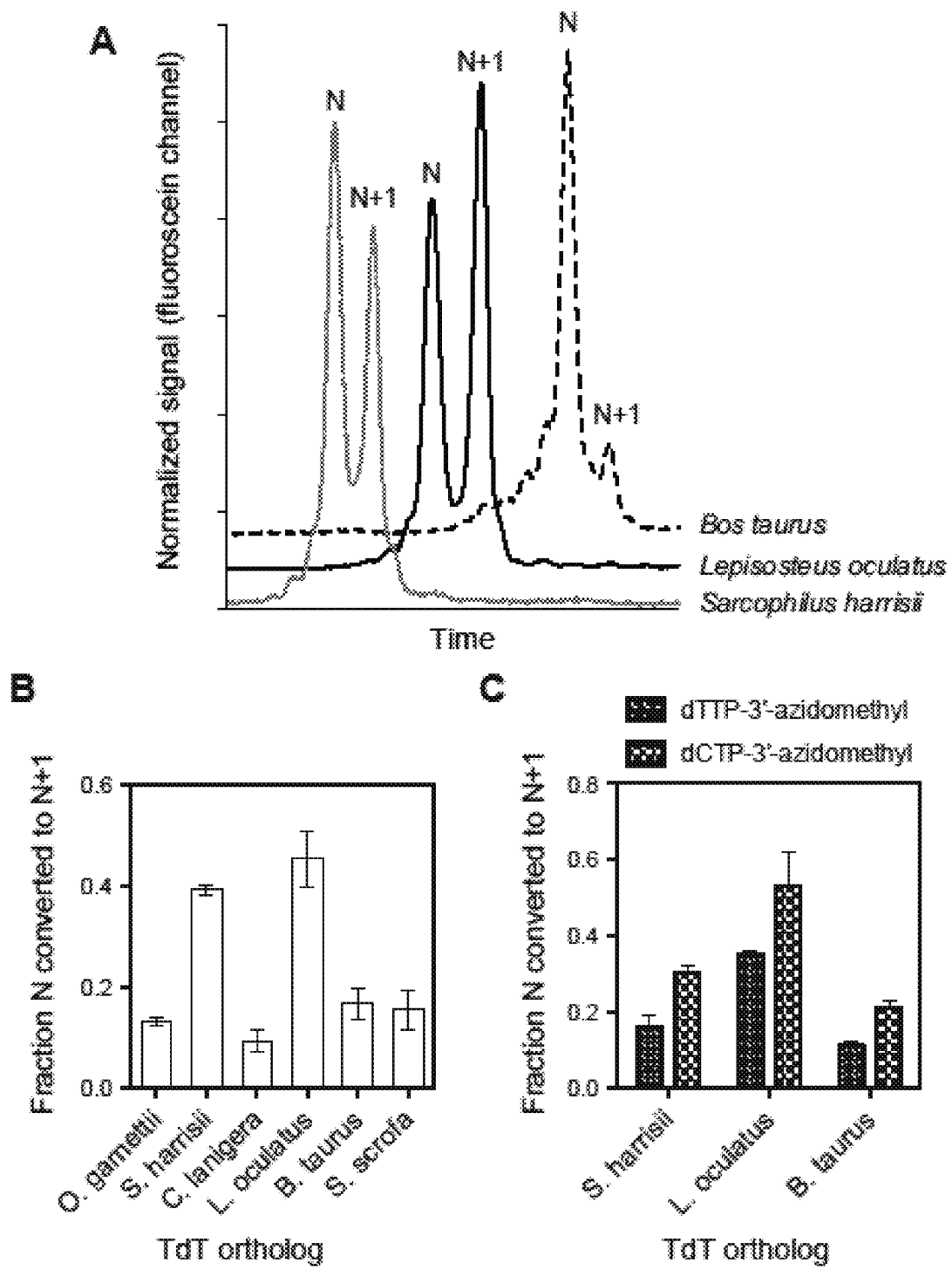
FIG. 3: Various TdT orthologs add a 3'-reversibly protected (3'-O-azidomethyl) nucleotide triphosphate to an initiator strand up to 3.8-fold faster than *Bos taurus* TdT. (A) A single-stranded DNA initiator was incubated with TdT with the indicated species for 60 min in the above mentioned buffer and reaction conditions. Reactions were then analysed by capillary electrophoresis and a subset of chromatograms are shown. (B) Fraction of DNA initiator strand converted to N+1 species (addition of 3'-O-azidomethyl dTTP) in one hour. (C) Three TdT orthologs were reacted with 3'-O-azidomethyl dTTP and 3'-O-azidomethyl dCTP for 20 min. *Lepisosteus oculatus* and *Sarcophilus harrisii* TdT consistently perform better compared to *Bos taurus* TdT. The ability for TdT orthologs to add both dTTP and dCTP nucleotide analogs demonstrate control of DNA sequence specificity.

In a further embodiment, the terminal deoxynucleotidyl transferase (TdT) enzyme comprises an amino acid sequence selected from SEQ ID NO: 1 or 2. Data are provided in Example 2 and FIG. 3, which demonstrate beneficial results over the natural, recombinant TdT enzyme from *Bos taurus*.

In an alternative embodiment, the terminal deoxynucleotidyl transferase (TdT) enzyme comprises an amino acid sequence selected from a modified derivative of SEQ ID NO: 6 (i.e. a non-natural, mutated derivative of SEQ ID NO: 6). The amino acid sequence of SEQ ID NO: 6 is the terminal deoxynucleotidyl transferase (TdT) sequence from *Bos taurus* (UniProt: P06526). *Bos taurus* (also known as cattle, or colloquially cows) are the most common type of large domesticated ungulates. They are a prominent modern member of the subfamily Bovinae, are the most widespread species of the genus *Bos*.

References herein to "TdT" refer to a terminal deoxynucleotidyl transferase (TdT) enzyme and include references to purified and recombinant forms of said enzyme. TdT Is also commonly known as DNTT (DNA nucleotidylexotransferase) and any such terms should be used interchangeably.

References herein to a "method of nucleic acid synthesis" include methods of synthesising lengths of DNA (deoxyribonucleic acid) or RNA (ribonucleic acid) wherein a strand of nucleic acid (n) is extended by adding a further nucleotide (n+1). In one embodiment, the nucleic acid is DNA. In an alternative embodiment, the nucleic acid is RNA.

References herein to "method of DNA synthesis" refer to a method of DNA strand synthesis wherein a DNA strand (n) is extended by adding a further nucleotide (n+1). The method described herein provides a novel use of the terminal deoxynucleotidyl transferases of the invention and 3'-reversibly blocked nucleotide triphosphates to sequentially add nucleotides in de novo DNA strand synthesis which has several advantages over the DNA synthesis methods currently known in the art.

Current synthetic methods for coupling nucleotides to form sequence-specific DNA have reached asymptotic length limits, therefore a new method of de novo DNA synthesis is required. Synthetic DNA synthesis methods also have the disadvantage of using toxic organic solvents and additives (e.g., acetonitrile, acetic anhydride, trichloroacetic acid, pyridine, etc.), which are harmful to the environment.

An alternative, enzymatic method of nucleic acid synthesis is desirable. Natural enzymes such as DNA polymerases are able to add 50,000 nucleotides before disassociation. However, DNA polymerases require a template strand, thereby defeating the purpose of de novo strand synthesis.

However, a DNA polymerase, called TdT, capable of template-independent DNA synthesis is found in vertebrates. Given a free 3'-end and nucleotide triphosphates, recombinant TdTs from *Bos taurus* and *Mus musculus* were shown to add ten to several hundred nucleotides onto the 3'-end of a DNA strand. As shown in a paper by Basu, M. et al. (*Biochem. Biophys. Res. Commun.* (1983) 111, 1105-1112) TdT will uncontrollably add nucleotide triphosphates to the 3'-end of a DNA strand. However, this uncontrolled addition is unsuitable for controlled de novo strand synthesis where a sequence-specific oligonucleotide is required. Thus, commercially available recombinant TdT is used primarily as a tool for molecular biologists to label DNA with useful chemical tags.

The present inventors have discovered several orthologs of *Bos taurus* TdT that, coupled with 3'-reversibly protected nucleotide triphosphates, are able to synthesise DNA in a controlled manner. *Bos taurus* TdT is not efficient at incorporating nucleotide triphosphates with 3'-protecting groups, likely due to steric issues in the TdT active site. Data is presented herein in Example 2 and FIG. 3 which demonstrates that orthologs of *Bos taurus* TdT, such as the purified recombinant TdTs of the first aspect of the invention (in particular SEQ ID NOS: 1 and 2), are far more efficient at incorporating 3'-OH blocked nucleotide triphosphates, thereby enabling template-independent, sequence-specific synthesis of nucleic acid strands.

This enzymatic approach means that the method has the particular advantage of being able to produce DNA strands beyond the 120-200 nucleotide limit of current synthetic DNA synthesis methods. Furthermore, this enzymatic method avoids the need to use strong organic solvents which may be harmful to the environment.

It will be understood that the term 'functional equivalent' refers to the polypeptides which are different to the exact sequence of the TdTs of the first aspect of the invention, but can perform the same function, i.e., catalyse the addition of a nucleotide triphosphate onto the 3'-end of a DNA strand in a template dependent manner.

In one embodiment, the terminal deoxynucleotidyl transferase (TdT) is a non-natural derivative of TdT, such as a functional fragment or homolog of the TdTs of the first aspect of the invention.

References herein to 'fragment' include, for example, functional fragments with a C-terminal truncation, or with an N-terminal truncation. Fragments are suitably greater than 10 amino acids in length, for example greater than 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 amino acids in length.

It will be appreciated that references herein to "homology" are to be understood as meaning the percentage identity between two protein sequences, e.g.: SEQ ID NO: X and SEQ ID NO: Y, which is the sum of the common amino acids between aligned sequences SEQ ID NO: X and SEQ ID NO: Y, divided by the shorter length of either SEQ ID NO: X or SEQ ID NO: Y, expressed as a percentage.

In one embodiment, the terminal deoxynucleotidyl transferase (TdT) has at least 25% homology with the TdTs of the first aspect of the invention, such as at least 30%, 40%, 50%, 55%, 60%, 65%, 70%, 75%, 80%, 85%, 90%, 95%, 96%, 97%, 98% or 99% homology.

According to a second aspect of the invention, there is provided a method of nucleic acid synthesis, which comprises the steps of:
  (a) providing an initiator sequence;
  (b) adding a 3'-blocked nucleotide triphosphate to said initiator sequence in the presence of a terminal deoxynucleotidyl transferase (TdT) as defined in the first aspect of the invention;
  (c) removal of all reagents from the initiator sequence;
  (d) cleaving the blocking group from the 3'-blocked nucleotide triphosphate in the presence of a cleaving agent;
  (e) removal of the cleaving agent.

In one embodiment, step (c) comprises removal of deoxynucleotide triphosphates and TdT, such as TdT. Thus, according to one particular aspect of the invention, there is provided a method of nucleic acid synthesis, which comprises the steps of:
  (a) providing an initiator sequence;
  (b) adding a 3'-blocked nucleotide triphosphate to said initiator sequence in the presence of a terminal deoxynucleotidyl transferase (TdT) as defined in the first aspect of the invention;
  (c) removal of TdT;
  (d) cleaving the blocking group from the 3'-blocked nucleotide triphosphate in the presence of a cleaving agent;
  (e) removal of the cleaving agent.

It will be understood that steps (b) to (e) of the method may be repeated multiple times to produce a DNA or RNA strand of a desired length. Therefore, in one embodiment, greater than 1 nucleotide is added to the initiator sequence, such as greater than 5, 10, 20, 30, 40, 50, 60, 70, 80, 90, 100, 110 or 120 nucleotides are added to the initiator sequence by repeating steps (b) to (e). In a further embodiment, greater than 200 nucleotides are added, such as greater than 300, 400, 500, 600, 700, 800, 900, 1000, 1250, 1500, 1750, 2000, 2250, 2500, 2750, 3000, 4000, 5000, 6000, 7000, 8000, 9000 or 10000 nucleotides.

3'-Blocked Nucleotide Triphosphates

References herein to 'nucleotide triphosphates' refer to a molecule containing a nucleoside (i.e. a base attached to a deoxyribose or ribose sugar molecule) bound to three phosphate groups. Examples of nucleotide triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of nucleotide triphosphates that contain ribose are: adenosine triphosphate (ATP), guanosine triphosphate (GTP), cytidine triphosphate (CTP) or uridine triphosphate (UTP). Other types of nucleosides may be bound to three phosphates to form nucleotide triphosphates, such as naturally occurring modified nucleosides and artificial nucleosides.

Therefore, references herein to '3'-blocked nucleotide triphosphates' refer to nucleotide triphosphates (e.g., dATP, dGTP, dCTP or dTTP) which have an additional group on the 3' end which prevents further addition of nucleotides, i.e., by replacing the 3'-OH group with a protecting group.

It will be understood that references herein to '3'-block', '3'-blocking group' or '3'-protecting group' refer to the group attached to the 3' end of the nucleotide triphosphate which prevents further nucleotide addition. The present method uses reversible 3'-blocking groups which can be removed by cleavage to allow the addition of further nucleotides. By contrast, irreversible 3'-blocking groups refer to dNTPs where the 3'-OH group can neither be exposed nor uncovered by cleavage.

There exist several documented reversible protecting groups, such as azidomethyl, aminoxy, and allyl, which can be applied to the method described herein. Examples of suitable protecting groups are described in *Greene's Protective Groups in Organic Synthesis*, (Wuts, P. G. M. & Greene, T. W. (2012) 4th Ed., John Wiley & Sons).

In one embodiment, the 3'-blocked nucleotide triphosphate is blocked by a reversible protecting group. In an alternative embodiment, the 3'-blocked nucleotide triphosphate is blocked by an irreversible protecting group.

Therefore, in one embodiment, the 3'-blocked nucleotide triphosphate is blocked by either a 3'-O-methyl, 3'-azido, 3'-O-azidomethyl, 3'-aminoxy or 3'-O-allyl group. In a further embodiment, the 3'-blocked nucleotide triphosphate is blocked by either a 3'-O-azidomethyl, 3'-aminoxy or 3'-O-allyl group. In an alternative embodiment, the 3'-blocked nucleotide triphosphate is blocked by either a 3'-O-methyl or 3'-azido group.

Cleaving Agent

References herein to 'cleaving agent' refer to a substance which is able to cleave the 3'-blocking group from the 3'-blocked nucleotide triphosphate.

The 3'-blocking groups described herein may all be quantitatively removed in aqueous solution with documented compounds which may be used as cleaving agents (for example, see: Wuts, P. G. M. & Greene, T. W. (2012) 4th Ed., John Wiley & Sons; Hutter, D. et al. (2010) *Nucleosides Nucleotides Nucleic Acids* 29, 879-895; EP 1560838 and U.S. Pat. No. 7,795,424).

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For instance, tris(2-carboxyethyl)phosphine (TCEP) can be used to cleave a 3'-O-azidomethyl group, palladium complexes can be used to cleave a 3'-O-allyl group, or sodium nitrite can be used to cleave a 3'-aminoxy group. Therefore, in one embodiment, the cleaving agent is selected from: tris(2-carboxyethyl) phosphine (TCEP), a palladium complex or sodium nitrite.

In one embodiment, the cleaving agent is added in the presence of a cleavage solution comprising a denaturant, such as urea, guanidinium chloride, formamide or betaine. The addition of a denaturant has the advantage of being able to disrupt any undesirable secondary structures in the DNA. In a further embodiment, the cleavage solution comprises one or more buffers. It will be understood by the person skilled in the art that the choice of buffer is dependent on the exact cleavage chemistry and cleaving agent required.

Initiator Sequences

References herein to an 'initiator sequence' refer to a short oligonucleotide with a free 3'-end which the 3'-blocked nucleotide triphosphate can be attached to. In one embodiment, the initiator sequence is a DNA initiator sequence. In an alternative embodiment, the initiator sequence is an RNA initiator sequence.

References herein to a 'DNA initiator sequence' refer to a small sequence of DNA which the 3'-blocked nucleotide triphosphate can be attached to, i.e. DNA will be synthesised from the end of the DNA initiator sequence.

In one embodiment, the initiator sequence is between 5 and 50 nucleotides long, such as between 5 and 30 nucleotides long (i.e. between 10 and 30), in particular between 5 and 20 nucleotides long (i.e., approximately 20 nucleotides long), more particularly 5 to 15 nucleotides long, for example 10 to 15 nucleotides long, especially 12 nucleotides long.

In one embodiment, the initiator sequence has the following sequence: 5'-CGTTAACATATT-3' (SEQ ID NO: 7).

In one embodiment, the initiator sequence is single-stranded. In an alternative embodiment, the initiator sequence is double-stranded. It will be understood by persons skilled in the art that a 3'-overhang (i.e., a free 3'-end) allows for efficient addition.

In one embodiment, the initiator sequence is immobilised on a solid support. This allows TdT and the cleaving agent to be removed (in steps (c) and (e), respectively) without washing away the synthesised nucleic acid. The initiator sequence may be attached to a solid support stable under aqueous conditions so that the method can be easily performed via a flow setup.

In one embodiment, the initiator sequence is immobilised on a solid support via a reversible interacting moiety, such as a chemically-cleavable linker, an antibody/immunogenic epitope, a biotin/biotin binding protein (such as avidin or streptavidin), or glutathione-GST tag. Therefore, in a further embodiment, the method additionally comprises extracting the resultant nucleic acid by removing the reversible interacting moiety in the initiator sequence, such as by incubating with proteinase K.

In a further embodiment, the initiator sequence is immobilised on a solid support via a chemically-cleavable linker, such as a disulfide, allyl, or azide-masked hemiaminal ether linker. Therefore, in one embodiment, the method additionally comprises extracting the resultant nucleic acid by cleaving the chemical linker through the addition of tris(2-carboxyethyl)phosphine (TCEP) or dithiothreitol (DTT) for a disulfide linker; palladium complexes for an allyl linker; or TCEP for an azide-masked hemiaminal ether linker.

In one embodiment, the resultant nucleic acid is extracted and amplified by polymerase chain reaction using the nucleic acid bound to the solid support as a template. The initiator sequence could therefore contain an appropriate forward primer sequence and an appropriate reverse primer could be synthesised.

In an alternative embodiment, the immobilised initiator sequence contains at least one restriction site. Therefore, in a further embodiment, the method additionally comprises extracting the resultant nucleic acid by using a restriction enzyme.

The use of restriction enzymes and restriction sites to cut nucleic acids in a specific location is well known in the art. The choice of restriction site and enzyme can depend on the desired properties, for example whether 'blunt' or 'sticky' ends are required. Examples of restriction enzymes include: AluI, BamHI, EcoRI, EcoRII, EcoRV, HaeII, HgaI, HindIII, HinfI, NotI, PstI, PvuII, SalI, Sau3A, ScaI, SmaI, TaqI and XbaI.

In an alternative embodiment, the initiator sequence contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Nucleic Acid Synthesis Method

In one embodiment, the terminal deoxynucleotidyl transferase (TdT) of the invention is added in the presence of an extension solution comprising one or more buffers (e.g., Tris or cacodylate), one or more salts (e.g., $Na^+$, $K^+$, $Mg^{2+}$, $Mn^{2+}$, $Cu^{2+}$, $Zn^{2+}$, $Co^{2+}$, etc., all with appropriate counterions, such as $Cl^-$) and inorganic pyrophosphatase (e.g., the *Saccharomyces cerevisiae* homolog). It will be understood that the choice of buffers and salts depends on the optimal enzyme activity and stability.

The use of an inorganic pyrophosphatase helps to reduce the build-up of pyrophosphate due to nucleotide triphosphate hydrolysis by TdT. Therefore, the use of an inorganic pyrophosphatase has the advantage of reducing the rate of (1) backwards reaction and (2) TdT strand dismutation.

Thus, according to a further aspect of the invention, there is provided the use of inorganic pyrophosphatase in a method of nucleic acid synthesis. Data is presented herein in Example 5 and FIG. 6 which demonstrates the benefit of the use of inorganic pyrophosphatase during nucleic acid synthesis. In one embodiment, the inorganic pyrophosphatase comprises purified, recombinant inorganic pyrophosphatase from *Saccharomyces cerevisiae*.

In one embodiment, step (b) is performed at a pH range between 5 and 10. Therefore, it will be understood that any buffer with a buffering range of pH 5-10 could be used, for example cacodylate, Tris, HEPES or Tricine, in particular cacodylate or Tris.

In one embodiment, step (d) is performed at a temperature less than 99° C., such as less than 95° C., 90° C., 85° C., 80° C., 75° C., 70° C., 65° C., 60° C., 55° C., 50° C., 45° C., 40° C., 35° C., or 30° C. It will be understood that the optimal temperature will depend on the cleavage agent utilised. The temperature used helps to assist cleavage and disrupt any secondary structures formed during nucleotide addition.

In one embodiment, steps (c) and (e) are performed by applying a wash solution. In one embodiment, the wash solution comprises the same buffers and salts as used in the extension solution described herein. This has the advantage of allowing the wash solution to be collected after step (c) and recycled as extension solution in step (b) when the method steps are repeated.

Figure 7:
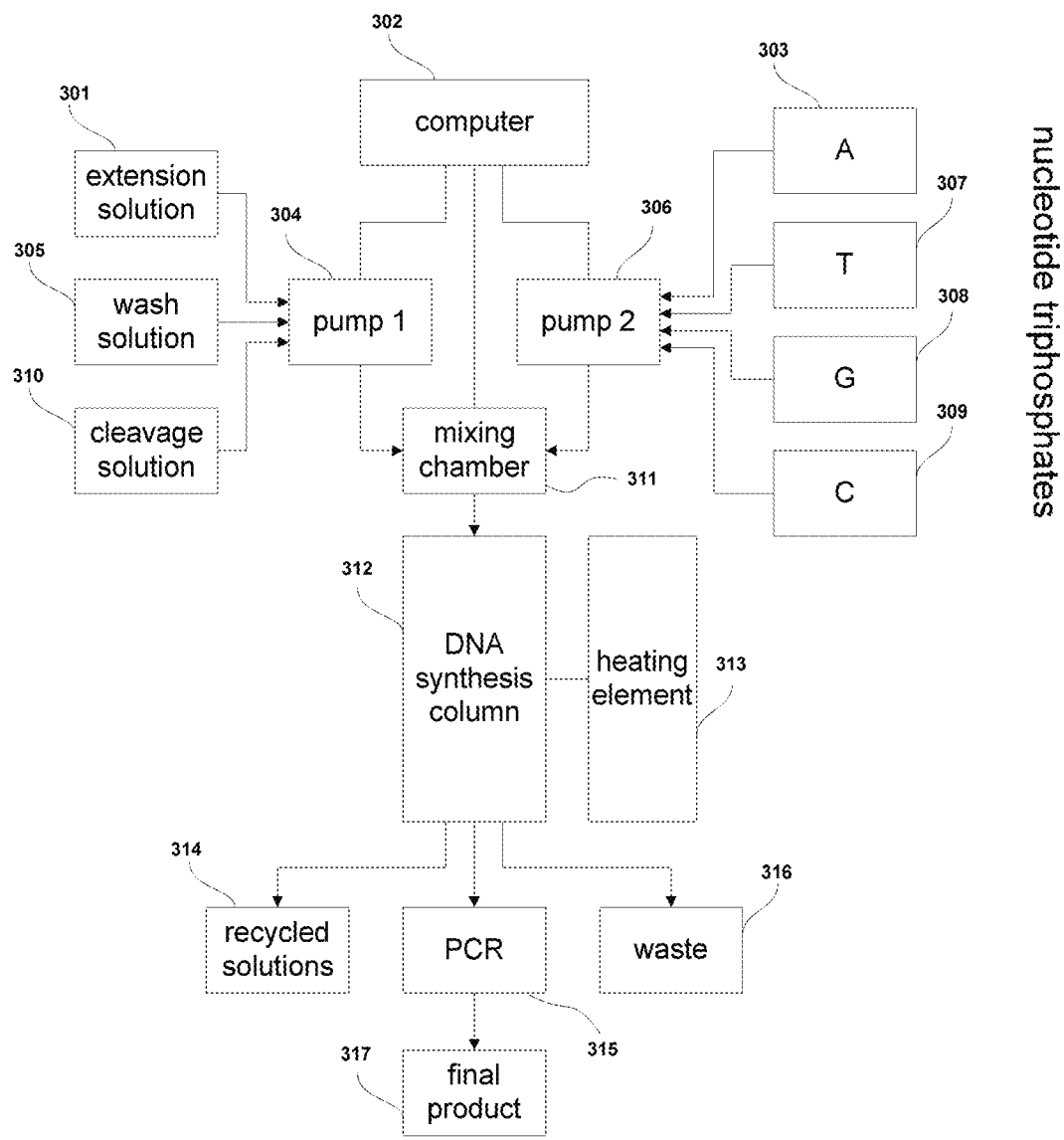
FIG. 7: Simplified schematic representation of a column-based flow instrument used in DNA synthesis. A computer (302) controls two pumps and a solution mixing chamber (311). Pump 1 (304) selectively pumps extension solution (301), wash solution (305) or cleavage solution (310) into the mixing chamber. Pump 2 (306) selectively pumps a single 3'-blocked nucleotide triphosphate (TP) solution containing either 3'-blocked A(adenine)TP (303), T(thymine)TP (307), G(guanine)TP (308), or C(cytosine)TP (309) into the chamber. The computer controlled mixing chamber then passes appropriate solution ratios from pump 1 and pump 2 into a column based DNA synthesis chamber (312). A heating element (313) ensures that the DNA synthesis column remains at the necessary temperature for the synthesis process to take place. Upon exiting the DNA synthesis chamber, the reaction solution either enters a recycling vessel (314) for future use, a waste vessel (316) or moves on to a polymerase chain reaction (PCR) step (315) for amplification of the resultant DNA. PCR completion leads to the final product (317).

In one embodiment, the method is performed within a flow instrument as shown in FIG. 7, such as a microfluidic or column-based flow instrument. The method described herein can easily be performed in a flow setup which makes the method simple to use. It will be understood that examples of commercially available DNA synthesisers (e.g., MerMade 192E from BioAutomation or H-8 SE from K&A) may be optimised for the required reaction conditions and used to perform the method described herein.

In one embodiment, the method is performed on a plate or microarray setup. For example, nucleotides may be individually addressed through a series of microdispensing nozzles using any applicable jetting technology, including piezo and thermal jets. This highly parallel process may be used to generate hybridization microarrays and is also amenable to DNA fragment assembly through standard molecular biology techniques.

In one embodiment, the method additionally comprises amplifying the resultant nucleic acid. Methods of DNA/RNA amplification are well known in the art. For example, in a further embodiment, the amplification is performed by polymerase chain reaction (PCR). This step has the advantage of being able to extract and amplify the resultant nucleic acid all in one step.

The template independent nucleic acid synthesis method described herein has the capability to add a nucleic acid sequence of defined composition and length to an initiator sequence. Therefore, it will be understood by persons skilled in the art, that the method described herein may be used as a novel way to introduce adapter sequences to a nucleic acid library.

If the initiator sequence is not one defined sequence, but instead a library of nucleic acid fragments (for example generated by sonication of genomic DNA, or for example messenger RNA) then this method is capable of de novo synthesis of 'adapter sequences' on every fragment. The installation of adapter sequences is an integral part of library preparation for next-generation library nucleic acid sequencing methods, as they contain sequence information allowing hybridisation to a flow cell/solid support and hybridisation of a sequencing primer.

Currently used methods include single-stranded ligation, however this technique is limited because ligation efficiency decreases strongly with increasing fragment length. Consequently, current methods are unable to attach sequences longer than 100 nucleotides in length. Therefore, the method described herein allows for library preparation in an improved fashion to that which is currently possible.

Therefore, in one embodiment, an adapter sequence is added to the initiator sequence. In a further embodiment, the initiator sequence may be a nucleic acid from a library of nucleic acid fragments.

Kits

According to a further aspect of the invention, there is provided the use of a kit in a method of nucleic acid synthesis, wherein said kit comprises a TdT as defined in the first or second aspects of the invention optionally in combination with one or more components selected from: an initiator sequence, one or more 3'-blocked nucleotide triphosphates, inorganic pyrophosphatase, such as purified, recombinant inorganic pyrophosphatase from *Saccharomyces cerevisiae*, and a cleaving agent; further optionally together with instructions for use of the kit in accordance with any of the methods defined herein.

Suitably a kit according to the invention may also contain one or more components selected from the group: an extension solution, a wash solution and/or a cleaving solution as defined herein; optionally together with instructions for use of the kit in accordance with any of the methods defined herein.

Use of 3'-Blocked Nucleotide Triphosphates

According to a further aspect of the invention, there is provided the use of a 3'-blocked nucleotide triphosphate in a method of template independent nucleic acid synthesis, wherein the 3'-blocked nucleotide triphosphate is selected from a compound of formula (I), (II), (III) or (IV):

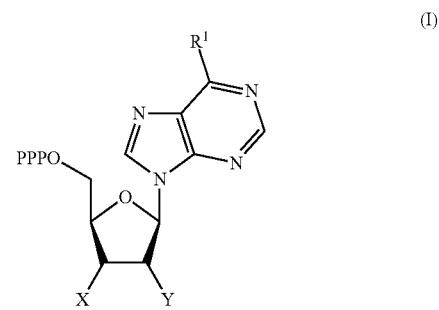

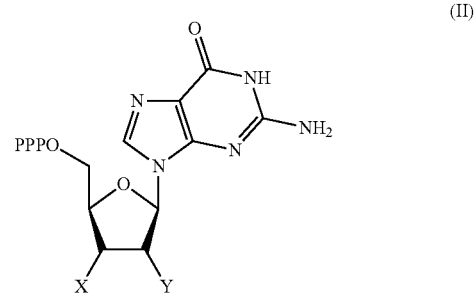

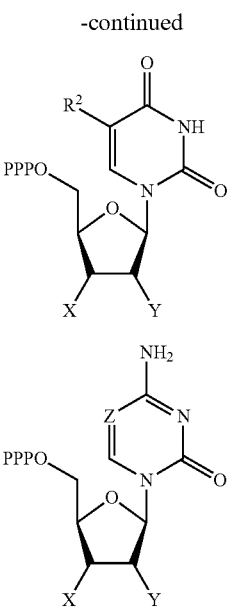

wherein
R¹ represents NR$^a$R$^b$, wherein R$^a$ and R$^b$ independently represent hydrogen or $C_{1-6}$ alkyl,
R² represents hydrogen, $C_{1-6}$ alkyl, $C_{1-6}$ alkoxy, COH or COOH.
X represents $C_{1-6}$ alkyl, NH₂, N₃ or —OR³,
R³ represents $C_{1-6}$ alkyl, CH₂N₃, NH₂ or allyl,
Y represents hydrogen, halogen or hydroxyl, and
Z represents CR⁴ or N, wherein R⁴ represents hydrogen, $C_{1-6}$ alkyl, $C_{1-6}$ alkoxy, COH or COOH.

References herein to a "template independent nucleic acid synthesis method" refer to a method of nucleic acid synthesis which does not require a template DNA/RNA strand, i.e. the nucleic acid can be synthesised de novo.

In one embodiment, the nucleic acid is DNA. References herein to a "template independent DNA synthesis method" refer to a method of DNA synthesis which does not require a template DNA strand, i.e. the DNA can be synthesised de novo. In an alternative embodiment, the nucleic acid is RNA.

It will be understood that PPP' in the structures shown herein represents a triphosphate group.

References to the term '$C_{1-6}$ alkyl' as used herein as a group or part of a group refers to a linear or branched saturated hydrocarbon group containing from 1 to 6 carbon atoms. Examples of such groups include methyl, ethyl, butyl, n-propyl, isopropyl and the like.

References to the term '$C_{1-6}$ alkoxy' as used herein refer to an alkyl group bonded to oxygen via a single bond (i.e. R—O). Such references include those with straight and branched alkyl chains containing 1 to 6 carbon atoms, such as methoxy (or methyloxy), ethyloxy, n-propyloxy, isopropyloxy, n-butyloxy and 2-methylpropyloxy.

References to the term 'allyl' as used herein refer to a substituent with the structural formula RCH₂—CH═CH₂, where R is the rest of the molecule. It consists of a methyl group (—CH₂—) attached to a vinyl group (—CH═CH₂).

References to the term 'COOH' or 'CO₂H' refer to a carboxyl group (or carboxy) which consists of a carbonyl (C═O) and a hydroxyl (O—H) group. References to the term 'COH' refer to a formyl group which consists of a carbonyl (C═O) group bonded to hydrogen.

The term 'N₃' (drawn structurally as —N═N⁺═N⁻) refers to an azido group.

In one embodiment, R$^a$ and R$^b$ both represent hydrogen (i.e. R¹ represents NH₂).

In an alternative embodiment, R$^a$ represents hydrogen and R$^b$ represents methyl (i.e. R¹ represents NHCH₃).

In one embodiment, R² represents hydrogen, methyl or methoxy. In a further embodiment, R² represents hydrogen. In an alternative embodiment, R² represents methyl. In a yet further alternative embodiment, R² represents methoxy.

In one embodiment, X represents —OR³, and R³ represents $C_{1-6}$ alkyl, CH₂N₃, NH₂ or allyl.

In an alternative embodiment, X represents $C_{1-6}$ alkyl (such as methyl) or N₃.

In one embodiment, Y represents hydrogen or hydroxyl.
In one embodiment, Y represents hydrogen.
In an alternative embodiment, Y represents hydroxyl.
In an alternative embodiment, Y represents halogen, such as fluorine.

In one embodiment, Z represents N.
In an alternative embodiment, Z represents CR⁴.

In one embodiment, R⁴ represents $C_{1-6}$ alkyl, $C_{1-6}$ alkoxy, COH or COOH.

In a further embodiment, R⁴ represents methoxy, COOH or COH. In a yet further embodiment, R⁴ represents methoxy. In an alternative embodiment, R⁴ represents COOH. In a yet further alternative embodiment, R⁴ represents COH.

In one embodiment, the 3'-blocked nucleotide triphosphate is selected from:

| Structure | Name | Example number |
|---|---|---|
| 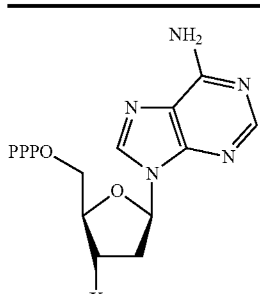 | Deoxyadenosine triphosphate | E1 |

-continued
| Structure | Name | Example number |
|---|---|---|
| 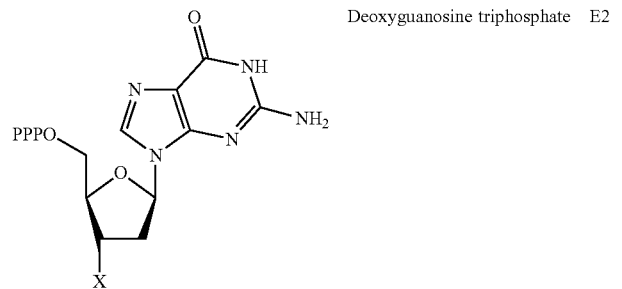 | Deoxyguanosine triphosphate | E2 |
| 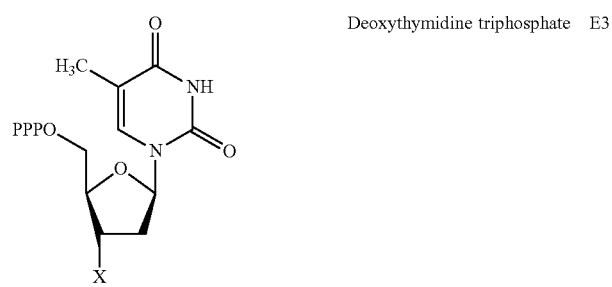 | Deoxythymidine triphosphate | E3 |
| 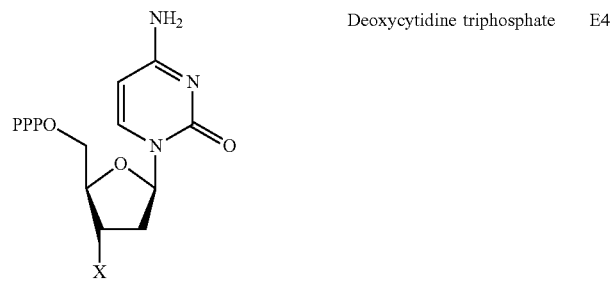 | Deoxycytidine triphosphate | E4 |
| 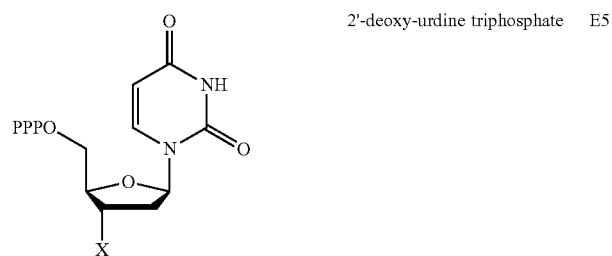 | 2'-deoxy-urdine triphosphate | E5 |
| 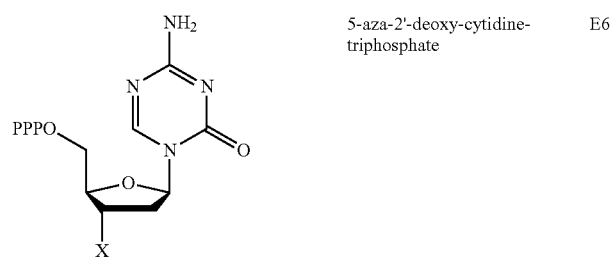 | 5-aza-2'-deoxy-cytidine-triphosphate | E6 |

| Structure | Name | Example number |
|---|---|---|
| [5-hydroxymethyl-deoxycytidine triphosphate structure] | 5-hydroxymethyl-deoxycytidine triphosphate | E7 |
| [5-carboxy-deoxycytidine triphosphate structure] | 5-carboxy-deoxycytidine triphosphate | E8 |
| [5-formyl-deoxycytidine triphosphate structure] | 5-formyl-deoxycytidine triphosphate | E9 |
| [N6-methyladenosine triphosphate structure] | N6-methyladenosine triphosphate | E10 |
| [5-hydroxymethyl-deoxyuridine triphosphate structure] | 5-hydroxymethyl-deoxy-uridine triphosphate | E11 | wherein 'X' is as defined hereinbefore.

The following studies and protocols illustrate embodiments of the methods described herein:

Comparative Example 1: Use of *Bos taurus* TdT to Add 3'-Irreversibly Blocked Nucleotide Triphosphates to a DNA Initiator A single-stranded DNA initiator (SEQ ID NO: 7) was incubated with 15 U *Bos taurus* TdT (Thermo Scientific), required salts (50 mM potassium acetate, 20 mM tris acetate pH 7.9, 1 mM cobalt chloride), and 3'-O-Methyl dTTP (TriLink) at 37° C. for up to one hour. The 3'-irreversibly blocked nucleotide triphosphate was at a concentration of 1 mM and the DNA initiator at 200 pM for a 1:5000 ratio to encourage nucleotide addition. The reaction was stopped with EDTA (0.5 M) at various intervals and the results are shown in FIG. 2(A).

The experiment was repeated with the exception that 3'-Azido dTTP was used as the 3'-irreversibly blocked nucleotide triphosphate instead of 3'-O-Methyl dTTP. The reaction was stopped with EDTA (0.5 M) at various intervals and the results are shown in FIG. 2(B).

Figure 2:
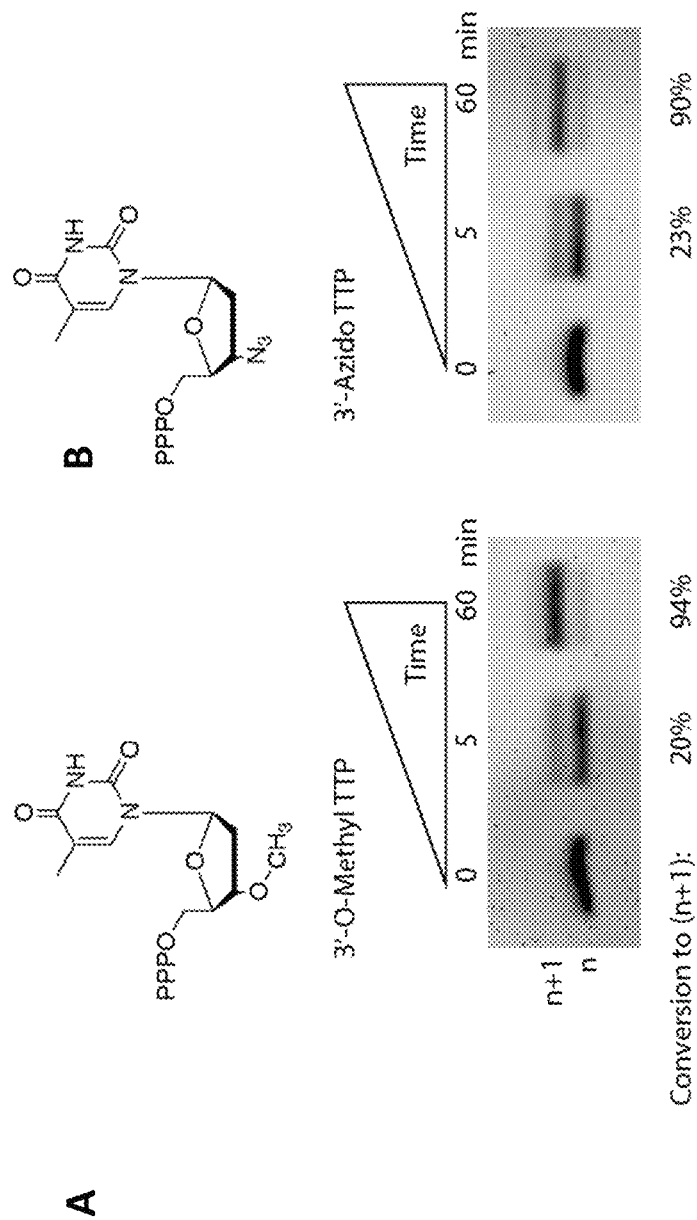
FIG. 2: TdT adds a 3'-irreversibly blocked nucleotide triphosphate to an initiator strand. (A) A single-stranded DNA initiator was incubated with 15 U *Bos taurus* TdT, required salts (50 mM potassium acetate, 20 mM tris acetate pH 7.9, 1 mM cobalt chloride), and 3'-O-Methyl dTTP at 37° C. for the indicated amount of time. The 3'-irreversibly blocked nucleotide triphosphate was at a concentration of 1 mM and the DNA initiator at 200 pM for a 1:5000 ratio to encourage nucleotide addition. The reaction was stopped with EDTA (0.5 M). (B) Similar to (A) with the exception that 3'-Azido dTTP was used as the 3'-blocked nucleotide triphosphate.

These studies show that the commercially available *Bos taurus* TdT adds irreversibly blocked nucleotides, specifically 3'-O-Methyl dTTP and 3'-Azido dTTP onto a DNA initiator strand (FIG. 2). Furthermore, the addition of a 3'-blocked nucleotide triphosphate to a single-stranded DNA initiator is completed to greater than 90% conversion of the n strand to the n+1 strand.

Example 2: Use of TdT Orthologs Other than *Bos Taurus* TdT for Controlled Template-Independent DNA Synthesis A single-stranded DNA initiator (SEQ ID NO: 7) was incubated with purified, recombinant TdT orthologs, required salts (50 mM potassium acetate, 20 mM tris acetate pH 7.9, 1.5 mM cobalt chloride, *Saccharomyces cerevisiae* inorganic pyrophosphatase), and 3'-O-azidomethyl dTTP at 37° C. for 60 min. The 3'-blocked nucleotide triphosphate was at a concentration of 1 mM and the DNA initiator at 200 nM and analysed via capillary electrophoresis as shown in FIG. 3(A). Reactions were quantified after 60 min and results are shown in FIG. 3(B).

The experiment was repeated with the exception that both 3'-O-azidomethyl dTTP and 3'-O-azidomethyl dCTP was used as the 3'-blocked nucleotide triphosphate. The reaction was stopped after 20 min and analysed via capillary electrophoresis. Quantified reactions are shown in FIG. 3(C).

*Bos taurus* TdT only efficiently adds irreversibly blocked nucleotides, which is not useful for controlled, enzymatic single-stranded DNA synthesis. This example demonstrates that naturally occurring TdT orthologs other than *Bos taurus* TdT perform significantly better at adding 3'-reversibly blocked nucleotide triphosphates. Better performance, which is judged by the N+1 addition rate (FIG. 3), results in longer achievable lengths and greater control of nucleic acid sequence specificity.

Example 3: Engineered TdT Orthologs Demonstrate Improved Function Over Wild-Type Proteins A single-stranded DNA initiator (SEQ ID NO: 7) was incubated with either a purified wild-type *Lepisosteus oculatus* TdT or a purified, recombinant engineered form of *Lepisosteus oculatus* TdT (SEQ ID NO: 8), required salts, cobalt chloride, *Saccharomyces cerevisiae* inorganic pyrophosphatase, and 3'-O-azidomethyl dTTP at 37° C. for 20 min.

The wild-type *Lepisosteus oculatus* TdT was outperformed by the engineered variant (SEQ ID NO: 8), as demonstrated by improved ability to convert the initiator strand of length n to a strand of length n+1, when supplied with 3'-reversibly blocked dCTP, dGTP or dTTP.

Example 4: Use of Engineered TdT Orthologs for Template-Independent and Sequence-Specific DNA Synthesis A single-stranded DNA initiator (SEQ ID NO: 7) was incubated with a purified, recombinant engineered form of *Lepisosteus oculatus* TdT, required salts, cobalt chloride, *Saccharomyces cerevisiae* inorganic pyrophosphatase, and 3'-O-azidomethyl dTTP at 37° C. for 10 min.

Figure 5:
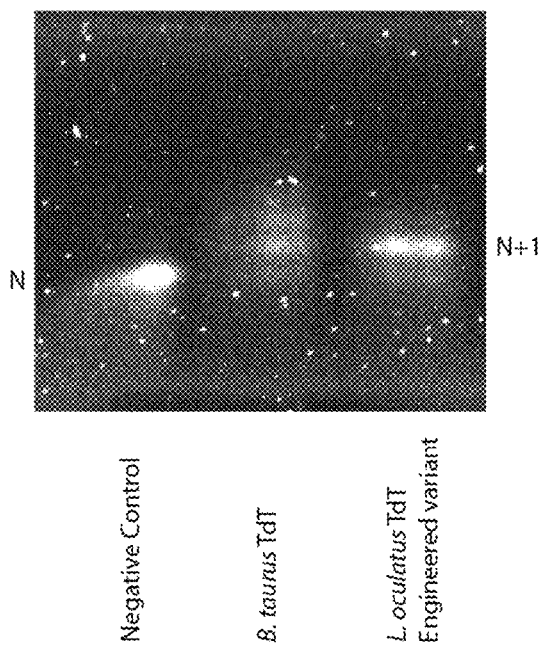
FIG. 5: An engineered variant of *Lepisosteus oculatus* shows vastly improved activity over the wild-type TdT (see FIG. 3) and commercially available *Bos taurus* TdT. TdT was incubated with a DNA initiator and a 3'-reversibly blocked dNTP in a similar fashion as previously described. *Bos taurus* TdT was outperformed by an engineered variant of *Lepisosteus oculatus* TdT, as demonstrated in the PAGE gel.

*Bos Taurus* TdT was outperformed by an engineered variant of *Lepisosteus oculatus* TdT, as demonstrated by the denaturing PAGE gel in FIG. 5. This example demonstrates an engineered form of *Lepisosteus oculatus* TdT incorporates 3'-reversibly blocked nucleotides (1) better than the wild-type *Lepisosteus oculatus* TdT, and (2) much better than *Bos Taurus* TdT (see FIGS. 2-5).

Figure 6:
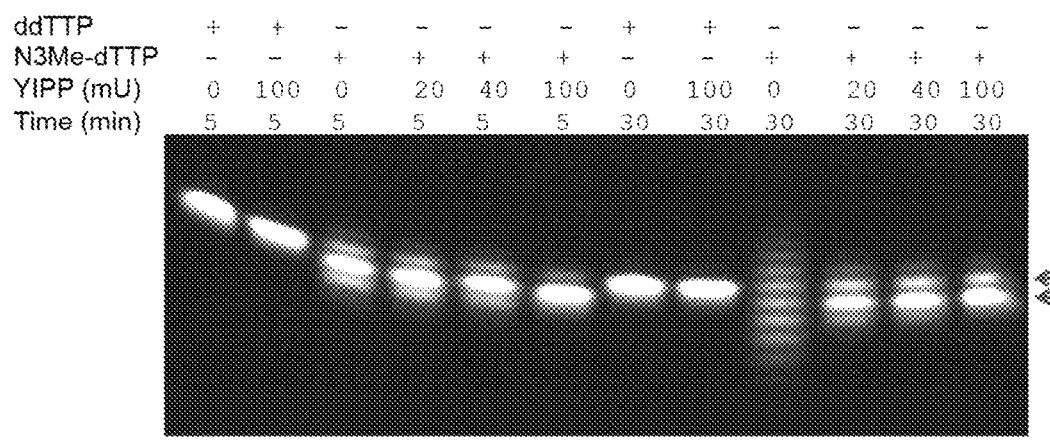
FIG. 6: Inorganic pyrophosphate is necessary for TdT-mediated, de novo sequence specific DNA synthesis. A nucleic acid initiator was incubated with and without *Saccharomyces cerevisiae* inorganic pyrophosphatase and *Bos taurus* TdT at 37° C. in 50 mM potassium acetate, 20 mM tris acetate pH 7.9, 1.5 mM cobalt chloride. 3'-O-azidomethyl dTTP ($N_3$Me-dTTP) was introduced at 1 mM and dideoxyTTP (ddTTP) was introduced at 100 μM. The reactions were analysed by PAGE. Without inorganic pyrophosphatase, strand dismutation predominates and catastrophic loss of sequence-specificity occurs.

Example 5: Use of Inorganic Pyrophosphatase to Control Nucleic Acid Sequence Specificity A single-stranded DNA initiator (SEQ ID NO: 7) was incubated with *Bos taurus* TdT at 37° C. for 60 min under the reaction buffer shown above with the exception that the concentration of *Saccharomyces cerevisiae* inorganic pyrophosphatase was varied. When dideoxyTTP (ddTTP) was used, the concentration of the NTP was 0.1 mM. Reactions were analysed by PAGE and are shown in FIG. 6.

The inorganic pyrophosphatase studies with TdT demonstrate that TdT-mediated DNA synthesis must utilise an inorganic pyrophosphatase in order to control nucleic acid sequence specificity.

Example 6: Example DNA Synthesis Method Using TdT

1. An immobilised single-stranded DNA initiator is exposed to the extension solution, which is composed of TdT; a base-specific 3'-blocked nucleotide triphosphate; inorganic pyrophosphatase (e.g., the *Saccharomyces cerevisiae* homolog); and any required buffers (e.g., tris(hydroxymethyl)aminomethane (Tris), cacodylate, or any buffer with a buffering range between pH 5-10) and salts (e.g., Na$^+$, K$^+$, Mg$^{2+}$, Mn$^{2+}$, Cu$^{2+}$, Zn$^{2+}$, Co$^{2+}$, etc., all with appropriate counterions, such as Cl$^-$) and reacted at optimised concentrations, times and temperatures. The 3'-blocked nucleotide triphosphate will contain one of the nitrogenous bases adenine, guanine, cytosine or thymine.

2. The extension mixture is then removed with wash mixture and recycled. Wash mixture is the extension mixture without TdT and the 3'-blocked nucleotide triphosphate.

3. The immobilised (n+1) DNA strand is treated with cleavage mixture composed of an appropriate buffer, denaturant (e.g., urea, guanidinium chloride, formamide, betaine, etc.), and cleavage agent (e.g., tris(2-carboxyethyl)phosphine (TCEP) to de-block a 3'-O-azidomethyl group; palladium complexes to de-block 3'-O-allyl group; or sodium nitrite to de-block the 3'-aminoxy group). The temperature can be raised up to 99° C. to assist in cleavage and disruption of secondary structures. The optimal temperature depends on the cleavage agent utilised.

4. The immobilised deblocked (n+1) DNA strand is treated with wash mixture to remove the cleavage mixture.

5. Cycles 1-4 are repeated with the base-specific 3'-blocked nucleotide triphosphate until the desired oligonucleotide sequence is achieved.

6. Once the desired sequence is achieved, polymerase chain reaction with primers specific to the DNA product is used to directly "extract" and amplify the product.

The invention claimed is:

1. A method of nucleic acid synthesis comprising:
   (a) providing an initiator oligonucleotide and
   (b) adding a 3'-blocked nucleoside triphosphate to said initiator oligonucleotide in the presence of a terminal deoxynucleotidyl transferase (TdT) enzyme comprising an amino acid sequence having at least 95% sequence identity to the full length sequence of any one of SEQ ID NOs: 1 to 5 and 8.

2. The method of nucleic acid synthesis according to claim 1, further comprising the steps of:
   (c) removal of all reagents from the initiator oligonucleotide;
   (d) cleaving the blocking group from the 3'-blocked nucleotide in the presence of a cleaving agent; and
   (e) removal of the cleaving agent.

3. The method as defined in claim 2, wherein greater than 1 nucleotide is added by repeating steps (b) to (e).

4. The method as defined in claim 2, wherein the 3'-blocked nucleotide is blocked by either a 3'-O-azidomethyl, 3'-aminoxy or 3'-O-allyl group.

5. The method as defined in claim 2, wherein the terminal deoxynucleotidyl transferase (TdT) is added in the presence of an extension solution comprising one or more buffers, such as Tris or cacodylate; one or more salts; and/or inorganic pyrophosphatase, such as purified, recombinant inorganic pyrophosphatase from *Saccharomyces cerevisiae*.

6. The method as defined in claim 2, wherein step (b) is performed at a pH range of between 5 and 10, step (d) is performed at a temperature less than 99° C., and/or steps (c) and (e) are performed by applying a wash solution.

7. The method as defined in claim 2, wherein the cleaving agent is a chemical cleaving agent, such as tris(2-carboxyethyl)phosphine (TCEP), a palladium complex and sodium nitrite, or the cleaving agent is an enzymatic cleaving agent.

8. The method as defined in claim 2, wherein the cleaving agent is added in the presence of a cleavage solution comprising a denaturant, such as urea, guanidinium chloride, formamide or betaine, and one or more buffers.

9. The method as defined in claim 2, wherein the method is performed within a flow instrument, such as a microfluidic or column-based flow instrument and/or is performed within a plate or microarray setup.

10. The method as defined in claim 2, wherein the initiator oligonucleotide is between 5 and 50 nucleotides long, such as between 10 and 30 nucleotides long, in particular approximately 20 nucleotides long and wherein the initiator oligonucleotide is immobilised on a solid support.

11. The method as defined in claim 10, wherein the reversible interacting moiety is a chemically-cleavable linker, such as a disulfide, allyl or azide-masked hemiaminal ether and the method further comprises a step of extracting the resultant nucleic acid by cleaving the chemically-cleavable linker, such as by the addition of tris(2-carboxyethyl) phosphine (TCEP), dithiothreitol (DTT) or a palladium complex.

12. The method as defined in claim 2, wherein the initiator oligonucleotide contains at least one restriction site and the method further comprises a step of extracting the resultant nucleic acid by using a restriction enzyme and/or the initiator oligonucleotide contains at least one uridine.

13. The method as defined in claim 2, further comprising a step of amplifying the resultant nucleic acid.

14. The method of claim 2, wherein the 3'-blocked nucleotide is a 3'-blocked nucleoside triphosphate selected from a compound of formula (I), (II), (III) or (IV):

(I)
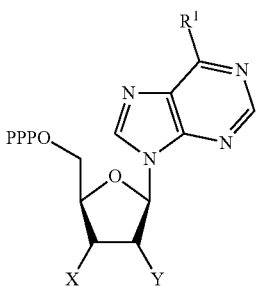

1p;2p (II)
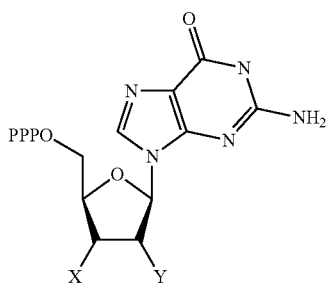

(III)
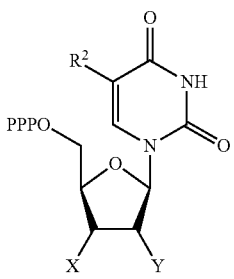

(IV)
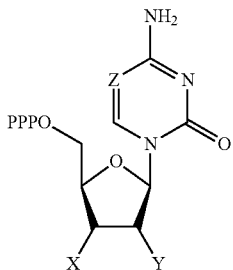

wherein
R$^1$ represents NR$^a$N$^b$, wherein R$^a$ and R$^b$ independently represent hydrogen or C$_{1-6}$ alkyl,
R$^2$ represents hydrogen, C$_{1-6}$ alkyl, C$_{1-6}$ alkoxy, COH or COOH,
X represents C$_{1-6}$ alkyl, NH$_2$, N$_3$ or —OR$^3$,
R$^3$ represents C$_{1-6}$ alkyl, CH$_2$N$_3$, NH$_2$ or allyl,
Y represents hydrogen, halogen or hydroxyl, and
Z represents CR$^4$ or N, wherein R$^4$ represents hydrogen, C$_{1-6}$ alkyl, C$_{1-6}$alkoxy, COH or COOH.

15. The method as defined in claim 14, wherein the 3'-blocked nucleotide is selected from deoxyadenosine triphosphate, deoxyguanosine triphosphate, deoxythymidine triphosphate, deoxycytidine triphosphate, 2'-deoxy-uridine triphosphate, 5-aza-2'-deoxy-cytidine-triphosphate, 5-hydroxymethyl-deoxycytidine triphosphate, 5-carboxy-deoxycytidine triphosphate, 5-formyl-deoxycytidine triphosphate, n6-methyladenosine triphosphate and 5-hydroxymethyl-deoxy-uridine triphosphate.

16. The method as defined in claim 1, wherein the TdT enzyme comprises an amino acid sequence having at least 95% sequence identity to the full length sequence of SEQ ID NO: 2.

17. The method as defined in claim 16, further comprising:
(c) removal of all reagents from the initiator oligonucleotide;
(d) cleaving the blocking group from the 3'-blocked nucleotide in the presence of a cleaving agent; and
(e) removal of the cleaving agent.

* * * * *

SEQUENCE LISTING

<160> NUMBER OF SEQ ID NOS: 8

<210> SEQ ID NO 1
<211> LENGTH: 517
<212> TYPE: PRT
<213> ORGANISM: Sarcophilus harrisii

<400> SEQUENCE: 1

```
Met His Arg Ile Arg Thr Thr Asp Ser Asp His Gly Lys Lys Arg Gln
1               5                   10                  15

Lys Lys Met Asp Ala Ile Ser Ser Lys Leu Tyr Glu Ile Lys Phe His
            20                  25                  30

Glu Phe Val Leu Phe Ile Leu Glu Lys Lys Met Gly Ala Thr Arg Arg
        35                  40                  45

Thr Phe Leu Met Asp Leu Ala Arg Lys Lys Gly Phe Arg Val Glu Ser
50                  55                  60

Glu Leu Ser Asn Ser Val Thr His Ile Val Ala Glu Asn Asn Ser Gly
65                  70                  75                  80

Ser Asp Val Leu Ala Trp Leu Glu Ala His Lys Leu Glu Thr Thr Ala
                85                  90                  95

His Phe Glu Leu Leu Asp Val Ser Trp Leu Ile Glu Cys Met Lys Val
            100                 105                 110

Gly Lys Pro Val Asp Thr Lys Gly Lys Tyr Gln Leu Val Glu Ser Ser
        115                 120                 125

Ile Ala Ser Ala Asn Pro Asp Pro Asn Glu Gly Met Leu Lys Ile Gln
130                 135                 140

Ser Pro Ala Met Asn Ala Ile Ser Pro Tyr Ala Cys Gln Arg Arg Thr
145                 150                 155                 160

Thr Leu Asn Asn His Asn Gln Arg Phe Thr Asp Ala Phe Glu Ile Leu
                165                 170                 175

Ala Lys Asn Tyr Glu Phe Arg Glu Asn His Gly His Cys Leu Thr Phe
            180                 185                 190

Leu Arg Ala Thr Ser Val Leu Lys Cys Leu Pro Phe Ala Ile Val Ser
        195                 200                 205

Met Lys Asp Ala Glu Gly Leu Pro Trp Ile Gly Asp Glu Val Lys Gly
210                 215                 220

Ile Met Glu Glu Ile Ile Glu Asp Gly Gln Ser Leu Glu Val Gln Ala
225                 230                 235                 240

Val Leu Asn Asp Glu Arg Tyr Gln Ala Phe Lys Leu Phe Thr Ser Val
                245                 250                 255

Phe Gly Val Gly Leu Lys Thr Ala Glu Lys Trp Tyr Arg Met Gly Phe
            260                 265                 270

Arg Thr Leu Ser Lys Ile Gln Ser Asp Lys Ser Leu Lys Phe Thr Lys
        275                 280                 285

Met Gln Lys Ala Gly Phe Leu Tyr Tyr Glu Asp Leu Ile Ser Cys Val
290                 295                 300

Ser Lys Ala Glu Ala Asp Ala Val Ser Leu Ile Val Lys Glu Ala Val
305                 310                 315                 320

Trp Thr Phe Leu Pro Asp Ala Leu Ile Thr Ile Thr Gly Gly Phe Arg
                325                 330                 335

Arg Gly Lys Glu Phe Gly His Asp Val Asp Phe Leu Ile Thr Ser Pro
            340                 345                 350

Gly Gly Glu Lys Glu Gln Val Asp Gln Leu Leu Gln Lys Val Thr Asn
        355                 360                 365
```

-continued

```
Leu Trp Glu Lys Gln Gly Leu Leu Tyr Tyr Asp Leu Met Glu Ser
    370                 375                 380

Thr Phe Glu Asp Leu Lys Leu Pro Ser Arg Lys Val Asp Ala Leu Asp
385                 390                 395                 400

His Phe Gln Lys Cys Phe Leu Ile Leu Lys Leu Tyr Cys Gln Arg Gly
                405                 410                 415

Asp Arg Ser Lys Trp Glu Gly Pro Gly Ser Asn Gly Leu Gln Thr
            420                 425                 430

Lys Asn Trp Lys Ala Ile Arg Val Asp Leu Val Val Cys Pro Tyr Asp
                435                 440                 445

Arg Tyr Ala Tyr Ala Leu Leu Gly Trp Ser Gly Ser Arg Gln Phe Glu
450                 455                 460

Arg Asp Leu Arg Arg Tyr Ala Thr His Glu Lys Lys Met Met Leu Asp
465                 470                 475                 480

Asn His Ala Leu Tyr Asp Lys Thr Lys Arg Thr Phe Leu Lys Ala Glu
                485                 490                 495

Ser Glu Glu Ile Phe Ser His Leu Gly Leu Glu Tyr Ile Glu Pro
            500                 505                 510

Trp Glu Arg Asn Ala
        515

<210> SEQ ID NO 2
<211> LENGTH: 494
<212> TYPE: PRT
<213> ORGANISM: Lepisosteus oculatus

<400> SEQUENCE: 2

Met Leu His Ile Pro Ile Phe Pro Pro Ile Lys Lys Arg Gln Lys Leu
1               5                   10                  15

Pro Glu Ser Arg Asn Ser Cys Lys Tyr Glu Val Lys Phe Ser Glu Val
                20                  25                  30

Ala Ile Phe Leu Val Glu Arg Lys Met Gly Ser Ser Arg Arg Lys Phe
            35                  40                  45

Leu Thr Asn Leu Ala Arg Ser Lys Gly Phe Arg Ile Glu Asp Val Leu
    50                  55                  60

Ser Asp Ala Val Thr His Val Val Ala Glu Asp Asn Ser Ala Asp Glu
65                  70                  75                  80

Leu Trp Gln Trp Leu Gln Asn Ser Ser Leu Gly Asp Leu Ser Lys Ile
                85                  90                  95

Glu Val Leu Asp Ile Ser Trp Phe Thr Glu Cys Met Gly Ala Gly Lys
            100                 105                 110

Pro Val Gln Val Glu Ala Arg His Cys Leu Val Lys Ser Cys Pro Val
        115                 120                 125

Ile Asp Gln Tyr Leu Glu Pro Ser Thr Val Glu Thr Val Ser Gln Tyr
    130                 135                 140

Ala Cys Gln Arg Arg Thr Thr Met Glu Asn His Asn Gln Ile Phe Thr
145                 150                 155                 160

Asp Ala Phe Ala Ile Leu Ala Glu Asn Ala Glu Phe Asn Glu Ser Glu
                165                 170                 175

Gly Pro Cys Leu Ala Phe Met Arg Ala Ala Ser Leu Leu Lys Ser Leu
            180                 185                 190

Pro His Ala Ile Ser Ser Ser Lys Asp Leu Glu Gly Leu Pro Cys Leu
        195                 200                 205

Gly Asp Gln Thr Lys Ala Val Ile Glu Asp Ile Leu Glu Tyr Gly Gln
    210                 215                 220
```

Cys Ser Lys Val Gln Asp Val Leu Cys Asp Asp Arg Tyr Gln Thr Ile
225                 230                 235                 240

Lys Leu Phe Thr Ser Val Phe Gly Val Gly Leu Lys Thr Ala Glu Lys
                245                 250                 255

Trp Tyr Arg Lys Gly Phe His Ser Leu Glu Glu Val Gln Ala Asp Asn
            260                 265                 270

Ala Ile His Phe Thr Lys Met Gln Lys Ala Gly Phe Leu Tyr Tyr Asp
                275                 280                 285

Asp Ile Ser Ala Ala Val Cys Lys Ala Glu Ala Gln Ala Ile Gly Gln
            290                 295                 300

Ile Val Glu Glu Thr Val Arg Leu Ile Ala Pro Asp Ala Ile Val Thr
305                 310                 315                 320

Leu Thr Gly Gly Phe Arg Arg Gly Lys Glu Cys Gly His Asp Val Asp
                325                 330                 335

Phe Leu Ile Thr Thr Pro Glu Met Gly Lys Glu Val Trp Leu Leu Asn
                340                 345                 350

Arg Leu Ile Asn Arg Leu Gln Asn Gln Gly Ile Leu Leu Tyr Tyr Asp
            355                 360                 365

Ile Val Glu Ser Thr Phe Asp Lys Thr Arg Leu Pro Cys Arg Lys Phe
370                 375                 380

Glu Ala Met Asp His Phe Gln Lys Cys Phe Ala Ile Ile Lys Leu Lys
385                 390                 395                 400

Lys Glu Leu Ala Ala Gly Arg Val Gln Lys Asp Trp Lys Ala Ile Arg
            405                 410                 415

Val Asp Phe Val Ala Pro Pro Val Asp Asn Phe Ala Phe Ala Leu Leu
                420                 425                 430

Gly Trp Thr Gly Ser Arg Gln Phe Glu Arg Asp Leu Arg Arg Phe Ala
            435                 440                 445

Arg His Glu Arg Lys Met Leu Leu Asp Asn His Ala Leu Tyr Asp Lys
            450                 455                 460

Thr Lys Lys Tyr Leu Lys Lys Thr Thr Asn Asn Tyr Leu Ala Leu
465                 470                 475                 480

Asn Asp Val Cys Ser Asp Leu Ser Glu Trp His Tyr Lys Gly
                485                 490

<210> SEQ ID NO 3
<211> LENGTH: 510
<212> TYPE: PRT
<213> ORGANISM: Chinchilla lanigera

<400> SEQUENCE: 3

Met Asp Pro Leu Gln Ala Ala His Ser Gly Pro Arg Lys Lys Arg Pro
1               5                   10                  15

Arg Gln Thr Gly Thr Leu Met Val Ser Ser Pro His Asp Val Arg Phe
                20                  25                  30

Gly Asp Leu Val Leu Phe Ile Leu Glu Lys Lys Met Gly Thr Thr Arg
                35                  40                  45

Arg Ala Phe Leu Met Glu Leu Ala Arg Arg Lys Gly Phe Arg Val Glu
            50                  55                  60

Asn Glu Leu Ser Asp Ser Val Thr His Ile Val Ala Glu Asn Asn Ser
65              70                  75                  80

Gly Asn Asp Val Leu Glu Trp Leu Gln Val Gln Asn Ile Gln Ala Ser
                85                  90                  95

Ser Arg Leu Glu Leu Leu Asp Val Ser Trp Leu Ile Glu Cys Met Gly

```
            100                 105                 110
Ala Gly Lys Pro Val Glu Met Thr Gly Lys His Gln Leu Leu Val Arg
            115                 120             125
Arg Asp Tyr Pro Ala Ser Pro Lys Pro Gly Pro Gln Lys Thr Pro Ser
        130                 135             140
Leu Ala Val Gln Lys Ile Ser Glu Tyr Ala Cys Gln Arg Arg Thr Thr
145                 150                 155                 160
Leu Asn Asn Cys Asn Cys Ile Phe Thr Asn Ala Phe Glu Ile Leu Ala
                165                 170                 175
Glu Asn Cys Glu Phe Arg Glu Asn Gly Ser Ser Tyr Val Thr Tyr Met
            180                 185                 190
Arg Ala Ala Ser Val Leu Lys Ser Leu Pro Phe Thr Ile Ile Ser Met
        195                 200                 205
Lys Asp Thr Glu Gly Ile Pro Cys Leu Gly Glu Lys Val Lys Cys Ile
        210                 215                 220
Ile Glu Glu Ile Ile Glu Asp Gly Glu Ser Ser Glu Val Asn Ala Val
225                 230                 235                 240
Leu Asn Asp Glu Arg Tyr Gln Ser Phe Lys Leu Phe Thr Ser Val Phe
                245                 250                 255
Gly Val Gly Leu Lys Thr Ser Glu Lys Trp Phe Arg Met Gly Phe Arg
            260                 265                 270
Ser Leu Asn Lys Ile Lys Ser Asp Lys Ser Leu Lys Phe Thr Arg Met
        275                 280                 285
Gln Lys Ala Gly Phe Leu Tyr Tyr Glu Asp Leu Val Ser Cys Val Thr
        290                 295                 300
Arg Ala Glu Ala Glu Ala Val Ser Met Leu Val Lys Glu Ala Val Trp
305                 310                 315                 320
Ala Phe Leu Pro Gly Ala Phe Ile Ser Met Thr Gly Gly Phe Arg Arg
                325                 330                 335
Gly Lys Glu Ile Gly His Asp Val Asp Phe Leu Ile Thr Ser Pro Glu
            340                 345                 350
Val Thr Glu Asp Glu Lys Gln Gln Leu Leu His Lys Val Ile Ser Leu
        355                 360                 365
Trp Glu Lys Lys Gly Leu Leu Leu Tyr Ser Asp Leu Val Glu Ser Thr
        370                 375                 380
Phe Glu Lys Leu Lys Leu Pro Ser Arg Lys Val Asp Ala Leu Asp His
385                 390                 395                 400
Phe Gln Lys Cys Phe Leu Ile Leu Lys Leu His His Gln Arg Val Asp
                405                 410                 415
Ser Asp Lys Ser Pro Gln Gln Gly Gly Lys Thr Trp Lys Ala Ile Arg
            420                 425                 430
Val Asp Leu Val Val Cys Pro Tyr Glu Arg Arg Ala Phe Ala Leu Leu
        435                 440                 445
Gly Trp Thr Gly Ser Arg Gln Phe Glu Arg Asp Leu Arg Arg Tyr Ala
        450                 455                 460
Thr His Glu Arg Lys Met Met Leu Asp Asn His Ala Leu Tyr Asp Lys
465                 470                 475                 480
Thr Lys Arg Ile Phe Leu Lys Ala Glu Ser Glu Glu Glu Ile Phe Ala
                485                 490                 495
His Leu Gly Leu Asp Tyr Ile Glu Pro Trp Glu Arg Asn Ala
            500                 505                 510

<210> SEQ ID NO 4
```

<211> LENGTH: 511
<212> TYPE: PRT
<213> ORGANISM: Otolemur garnettii

<400> SEQUENCE: 4

```
Met Asp Pro Leu His Met Ala His Ser Gly Pro Arg Lys Lys Arg Pro
1               5                   10                  15

Arg Gln Thr Ala Ala Ser Met Val Ser Thr Pro Gln Asp Ile Lys Phe
            20                  25                  30

Arg Asp Leu Val Leu Phe Ile Leu Glu Lys Lys Met Gly Thr Thr Arg
        35                  40                  45

Arg Thr Phe Leu Met Glu Leu Ala Arg Thr Lys Gly Phe Arg Val Glu
    50                  55                  60

Asn Glu Phe Ser Asp Ser Val Thr His Ile Ile Ala Glu Asn Asn Ser
65                  70                  75                  80

Gly Ser Asp Val Leu Glu Trp Ile Gln Val Gln Lys Ile Lys Ala Gly
                85                  90                  95

Ser Gln Met Glu Val Leu Asp Val Ser Trp Leu Ile Glu Cys Met Arg
            100                 105                 110

Ala Gly Lys Pro Val Glu Met Thr Gly Lys His Gln Leu Val Val Arg
        115                 120                 125

Gly Asp Tyr Ser Pro Ser Pro Asn Pro Ala Pro Gln Lys Thr Pro Pro
    130                 135                 140

Leu Ala Val Gln Lys Ile Ser Gln Tyr Ala Cys Gln Arg Arg Thr Thr
145                 150                 155                 160

Leu Asn Asn Cys Asn His Ile Phe Thr Asp Ala Phe Glu Ile Met Ala
                165                 170                 175

Glu Asn Tyr Glu Phe Arg Glu Asn Gly Tyr Ser Ala Ala Phe Met
            180                 185                 190

Arg Ala Ala Ser Val Leu Lys Ser Leu Pro Phe Thr Ile Ile Ser Met
        195                 200                 205

Lys Asp Thr Glu Gly Val Pro Cys Leu Gly Asp Asn Val Lys Cys Ile
    210                 215                 220

Ile Glu Glu Ile Ile Glu Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Ile Arg Ser Asp Lys Ser Leu Arg Phe Thr Arg Met
        275                 280                 285

Gln Gln Ala Gly Phe Leu Tyr Tyr Glu Asp Leu Val Ser Cys Val Thr
    290                 295                 300

Arg Ala Glu Ala Glu Ala Val Gly Val Leu Val Lys Glu Ala Val Arg
305                 310                 315                 320

Ala Phe Leu Pro Asp Ala Phe Val Thr Met Thr Gly Gly Phe Arg Arg
                325                 330                 335

Gly Lys Asn Ile Gly His Asp Val Asp Phe Leu Ile Thr Ser Pro Gly
            340                 345                 350

Ser Thr Glu Glu Glu Gln Gln Leu Leu His Lys Ile Met Asp Leu
        355                 360                 365

Trp Glu Lys Lys Gly Leu Leu Leu Tyr Cys Asp Leu Val Glu Ser Thr
    370                 375                 380

Phe Glu Lys Leu Lys Leu Pro Ser Arg Lys Val Asp Ala Leu Asp His
```

```
                385                 390                 395                 400
        Phe Gln Lys Cys Phe Leu Ile Phe Lys Leu His His Gln Arg Val Val
                        405                 410                 415

Asp Ser Glu Gln Ser Asn Gln Gln Glu Gly Lys Thr Trp Lys Ala Ile
                        420                 425                 430

Arg Val Asp Leu Val Met Cys Pro Tyr Glu Arg Arg Ala Tyr Ala Leu
                        435                 440                 445

Leu Gly Trp Thr Gly Ser Arg Gln Phe Glu Arg Asp Leu Arg Arg Tyr
                        450                 455                 460

Ala Thr His Glu Arg Lys Met Ile Leu Asp Asn His Gly Leu Trp Asp
        465                 470                 475                 480

Lys Thr Lys Arg Ile Phe Leu Lys Ala Glu Ser Glu Glu Ile Phe
                        485                 490                 495

Ala His Leu Gly Leu Asp Tyr Ile Glu Pro Trp Glu Arg Asn Ala
                        500                 505                 510

<210> SEQ ID NO 5
<211> LENGTH: 510
<212> TYPE: PRT
<213> ORGANISM: Sus scrofa

<400> SEQUENCE: 5

Met Asp Pro Pro Gln Thr Val Pro Ser Ser Pro Arg Lys Lys Arg Pro
        1               5                   10                  15

Arg Gln Val Gly Ala Ser Met Ala Ser Pro Ala His Asn Ile Lys Phe
                        20                  25                  30

Arg Glu Leu Val Leu Phe Ile Leu Glu Lys Lys Met Gly Thr Thr Arg
                        35                  40                  45

Arg Thr Phe Leu Met Glu Leu Ala Arg Arg Lys Gly Phe Arg Val Glu
                        50                  55                  60

Asn Glu Leu Ser Asp Ser Val Thr His Ile Val Ala Glu Asn Asn Ser
        65                  70                  75                  80

Gly Ser Glu Val Leu Glu Trp Leu Gln Ala Gln Lys Ile Arg Ala Ser
                        85                  90                  95

Ser Gln Leu Thr Leu Leu Asp Val Ser Trp Leu Ile Glu Ser Met Gly
                        100                 105                 110

Ala Gly Lys Pro Val Glu Met Thr Gly Lys His Gln Leu Val Val Arg
                        115                 120                 125

Thr Asp Cys Ser Ala Ser Pro Ser Pro Gly Ser Gln Asn Thr Leu Pro
        130                 135                 140

Pro Ala Val Lys Lys Ile Ser Gln Tyr Ala Cys Gln Arg Arg Thr Thr
        145                 150                 155                 160

Leu Asn Asn Cys Asn His Ile Phe Thr Asp Ala Phe Glu Val Leu Ala
                        165                 170                 175

Glu Asn Tyr Glu Phe Arg Glu Asn Glu Thr Phe Cys Leu Ala Phe Met
                        180                 185                 190

Arg Ala Ala Ser Val Leu Lys Ser Leu Pro Phe Thr Ile Ile Ser Met
                        195                 200                 205

Lys Asp Thr Glu Gly Ile Pro Cys Leu Gly Asp Lys Val Lys Cys Val
                        210                 215                 220

Ile Glu Glu Ile Ile Glu Asp Gly Glu Ser Ser Glu Val Lys Ala Val
        225                 230                 235                 240

Leu Asn Asp Glu Arg Tyr Gln Ser Phe Lys Leu Phe Thr Ser Val Phe
                        245                 250                 255
```

Gly Val Gly Leu Lys Thr Ser Glu Arg Trp Phe Arg Met Gly Phe Arg
            260                 265                 270

Ser Leu Ser Lys Ile Arg Ser Asp Lys Thr Leu Lys Phe Thr Arg Met
            275                 280                 285

Gln Lys Ala Gly Phe Leu Tyr Tyr Glu Asp Leu Val Ser Cys Val Thr
            290                 295                 300

Arg Ala Glu Ala Glu Ala Val Gly Val Leu Val Lys Glu Ala Val Gln
305                 310                 315                 320

Ala Phe Leu Pro Asp Ala Phe Val Thr Met Thr Gly Gly Phe Arg Arg
            325                 330                 335

Gly Lys Lys Met Gly His Asp Val Asp Phe Leu Ile Thr Ser Pro Gly
            340                 345                 350

Ser Thr Asp Asp Glu Glu Gln Gln Leu Leu Pro Lys Val Val Asn Leu
            355                 360                 365

Trp Glu Arg Glu Gly Leu Leu Leu Tyr Cys Asp Leu Val Glu Ser Thr
            370                 375                 380

Leu Glu Lys Ser Lys Leu Pro Ser Arg Asn Val Asp Ala Leu Asp His
385                 390                 395                 400

Phe Gln Lys Cys Phe Leu Ile Leu Lys Leu His His Gln Arg Val Asp
            405                 410                 415

Ser Gly Met Ser Ser Gln Gln Glu Gly Lys Thr Trp Lys Ala Ile Arg
            420                 425                 430

Val Asp Leu Val Met Cys Pro Tyr Glu Leu Arg Ala Phe Ala Leu Leu
            435                 440                 445

Gly Trp Thr Gly Ser Arg Gln Phe Glu Arg Asp Leu Arg Arg Tyr Ala
            450                 455                 460

Thr His Glu Arg Lys Met Ile Leu Asp Asn His Ala Leu Tyr Asp Lys
465                 470                 475                 480

Thr Lys Arg Ile Phe Leu Lys Ala Glu Ser Glu Glu Ile Phe Ala
            485                 490                 495

His Leu Gly Leu Asp Tyr Leu Glu Pro Trp Glu Arg Asn Ala
            500                 505                 510

<210> SEQ ID NO 6
<211> LENGTH: 509
<212> TYPE: PRT
<213> ORGANISM: Bos taurus

<400> SEQUENCE: 6

Met Asp Pro Leu Cys Thr Ala Ser Ser Gly Pro Arg Lys Lys Arg Pro
1               5                   10                  15

Arg Gln Val Gly Ala Ser Met Ala Ser Pro Pro His Asp Ile Lys Phe
            20                  25                  30

Gln Asn Leu Val Leu Phe Ile Leu Glu Lys Lys Met Gly Thr Thr Arg
            35                  40                  45

Arg Asn Phe Leu Met Glu Leu Ala Arg Arg Lys Gly Phe Arg Val Glu
            50                  55                  60

Asn Glu Leu Ser Asp Ser Val Thr His Ile Val Ala Glu Asn Asn Ser
65                  70                  75                  80

Gly Ser Glu Val Leu Glu Trp Leu Gln Val Gln Asn Ile Arg Ala Ser
            85                  90                  95

Ser Gln Leu Glu Leu Leu Asp Val Ser Trp Leu Ile Glu Ser Met Gly
            100                 105                 110

Ala Gly Lys Pro Val Glu Ile Thr Gly Lys His Gln Leu Val Val Arg
            115                 120                 125

Thr Asp Tyr Ser Ala Thr Pro Asn Pro Gly Phe Gln Lys Thr Pro Pro
            130                 135                 140

Leu Ala Val Lys Lys Ile Ser Gln Tyr Ala Cys Gln Arg Lys Thr Thr
145                 150                 155                 160

Leu Asn Asn Tyr Asn His Ile Phe Thr Asp Ala Phe Glu Ile Leu Ala
                165                 170                 175

Glu Asn Ser Glu Phe Lys Glu Asn Glu Val Ser Tyr Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Asp Lys Val Lys Cys Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Ser Leu Ser Lys Ile Met Ser Asp Lys Thr Leu Lys Phe Thr Lys Met
        275                 280                 285

Gln Lys Ala Gly Phe Leu Tyr Tyr Glu Asp Leu Val Ser Cys Val Thr
290                 295                 300

Arg Ala Glu Ala Glu Ala Val Gly Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Ile Gly His Asp Val Asp Phe Leu Ile Thr Ser Pro Gly
            340                 345                 350

Ser Ala Glu Asp Glu Glu Gln Leu Leu Pro Lys Val Ile Asn Leu Trp
        355                 360                 365

Glu Lys Lys Gly Leu Leu Leu Tyr Tyr Asp Leu Val Glu Ser Thr Phe
370                 375                 380

Glu Lys Phe Lys Leu Pro Ser Arg Gln Val Asp Thr Leu Asp His Phe
385                 390                 395                 400

Gln Lys Cys Phe Leu Ile Leu Lys Leu His His Gln Arg Val Asp Ser
                405                 410                 415

Ser Lys Ser Asn Gln Gln Glu Gly Lys Thr Trp Lys Ala Ile Arg Val
            420                 425                 430

Asp Leu Val Met Cys Pro Tyr Glu Asn Arg Ala Phe Ala Leu Leu Gly
        435                 440                 445

Trp Thr Gly Ser Arg Gln Phe Glu Arg Asp Ile Arg Arg Tyr Ala Thr
450                 455                 460

His Glu Arg Lys Met Met Leu Asp Asn His Ala Leu Tyr Asp Lys Thr
465                 470                 475                 480

Lys Arg Val Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 7
<211> LENGTH: 12
<212> TYPE: DNA
<213> ORGANISM: Artificial Sequence
<220> FEATURE:

<223> OTHER INFORMATION: Synthetic Oligonucleotide

<400> SEQUENCE: 7
cgttaacata tt                                                             12

<210> SEQ ID NO 8
<211> LENGTH: 494
<212> TYPE: PRT
<213> ORGANISM: Artificial Sequence
<220> FEATURE:
<223> OTHER INFORMATION: Synthetic Polypeptide

<400> SEQUENCE: 8

```
Met Leu His Ile Pro Ile Phe Pro Pro Ile Lys Lys Arg Gln Lys Leu
1               5                   10                  15

Pro Glu Ser Arg Asn Ser Cys Lys Tyr Glu Val Lys Phe Ser Glu Val
            20                  25                  30

Ala Ile Phe Leu Val Glu Arg Lys Met Gly Ser Ser Arg Arg Lys Phe
        35                  40                  45

Leu Thr Asn Leu Ala Arg Ser Lys Gly Phe Arg Ile Glu Asp Val Leu
    50                  55                  60

Ser Asp Ala Val Thr His Val Ala Glu Asn Asn Ser Ala Asp Glu
65                  70                  75                  80

Leu Leu Gln Trp Leu Gln Asn Ser Ser Leu Gly Asp Leu Ser Lys Ile
                85                  90                  95

Glu Val Leu Asp Ile Ser Trp Phe Thr Glu Cys Met Gly Ala Gly Lys
            100                 105                 110

Pro Val Gln Val Glu Ala Arg His Cys Leu Val Lys Ser Cys Pro Val
        115                 120                 125

Ile Asp Gln Tyr Leu Glu Pro Ser Thr Val Thr Val Ser Gln Tyr
    130                 135                 140

Ala Cys Gln Arg Arg Thr Thr Met Glu Asn His Asn Gln Ile Phe Thr
145                 150                 155                 160

Asp Ala Phe Ala Ile Leu Ala Glu Asn Ala Glu Phe Asn Glu Ser Glu
                165                 170                 175

Gly Pro Cys Leu Ala Phe Met Arg Ala Ala Ser Leu Leu Lys Ser Leu
            180                 185                 190

Pro His Ala Ile Ser Ser Lys Asp Leu Glu Gly Leu Pro Cys Leu
        195                 200                 205

Gly Asp Gln Thr Lys Ala Val Ile Glu Asp Ile Leu Glu Tyr Gly Gln
    210                 215                 220

Cys Ser Lys Val Gln Asp Val Leu Cys Asp Asp Arg Tyr Gln Thr Ile
225                 230                 235                 240

Lys Leu Phe Thr Ser Val Phe Gly Val Gly Leu Arg Thr Ala Glu Lys
                245                 250                 255

Trp Tyr Arg Lys Gly Phe His Ser Leu Glu Glu Val Gln Ala Asp Asn
            260                 265                 270

Ala Ile His Phe Thr Lys Met Gln Lys Ala Gly Phe Leu Tyr Tyr Asp
        275                 280                 285

Asp Ile Ser Ala Ala Val Cys Lys Ala Glu Ala Gln Ala Ile Gly Gln
    290                 295                 300

Ile Val Glu Glu Thr Val Arg Leu Ile Ala Pro Asp Ala Ile Val Thr
305                 310                 315                 320

Leu Thr Gly Gly Phe Arg Arg Gly Lys Glu Cys Gly His Asp Val
                325                 330                 335
```

```
Phe Leu Ile Thr Thr Pro Glu Met Gly Lys Glu Val Trp Leu Leu Asn
            340             345                 350

Arg Leu Ile Asn Arg Leu Gln Asn Gln Gly Ile Leu Leu Tyr Tyr Asp
        355             360             365

Ile Val Glu Ser Thr Phe Asp Lys Thr Arg Leu Pro Cys Arg Lys Phe
        370             375             380

Glu Ala Met Asp His Phe Gln Lys Cys Phe Ala Ile Ile Lys Leu Lys
385                 390             395                     400

Lys Glu Leu Ala Ala Gly Arg Val Gln Lys Asp Trp Lys Ala Ile Arg
                405             410             415

Val Asp Phe Val Ala Pro Pro Val Asp Asn Phe Ala Phe Ala Leu Leu
                420             425             430

Gly Trp Thr Gly Ser Arg Gln Phe Glu Arg Asp Leu Arg Arg Phe Ala
            435             440             445

Arg His Glu Arg Lys Met Leu Leu Asp Asn His Ala Leu Tyr Asp Lys
        450             455             460

Thr Lys Lys Ile Phe Leu Pro Ala Lys Thr Glu Glu Asp Ile Phe Ala
465             470             475                     480

His Leu Gly Leu Asp Tyr Ile Asp Pro Trp Gln Arg Asn Ala
                485             490
```